United States Patent [19]

Achiwa

[11] Patent Number: 5,234,821
[45] Date of Patent: Aug. 10, 1993

[54] PROCESS FOR PREPARING 1,4 DIHYDROPYRIDINE COMPOUNDS

[76] Inventor: Kazuo Achiwa, 15-5, Kamikutsunoya-cho, Shizuoka-shi, Shizuoka, Japan

[21] Appl. No.: 752,796

[22] Filed: Aug. 30, 1991

[30] Foreign Application Priority Data

Sep. 1, 1990 [JP] Japan ................................ 2-231345
Feb. 28, 1991 [JP] Japan ................................ 3-59582

[51] Int. Cl.$^5$ .................. C07D 211/90; C12P 17/12; C12P 41/00
[52] U.S. Cl. ..................................... 435/41; 435/195; 435/197; 435/280; 546/321
[58] Field of Search ................. 435/41, 195, 197, 280

[56] References Cited

PUBLICATIONS

Conrad et al. *Encyclopedia of Polymer Science and Technology*, vol. 6, p. 49.
Cambou et al, *Biotechnology and Bioengineering*, vol. XXVI, pp. 1449-1454 (1984).
Kajino et al, *Chem. Pharm. Bull*, vol. 37 pp. 2225-2228, (1989).
Tamazawa et al, *J. Med. Chem.*, vol. 29, pp. 2504-2511, (1986).
*Tetrahedron Letters*, vol. 32, No. 29, pp. 3465-3468 (Jul. 15, 1991).

*Primary Examiner*—C. Warren Ivy
*Assistant Examiner*—Zinna N. Davis
*Attorney, Agent, or Firm*—Sughrue, Mion, Zinn, Macpeak & Seas

[57] ABSTRACT

A 1,4-dihydropyridine derivative represented by formula (I):

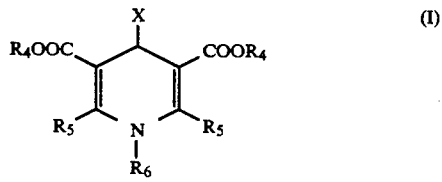

wherein X represents an alkyl group, or a group of

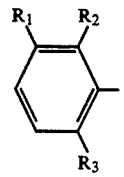

in which $R_1$, $R_2$, and $R_3$ may be the same or different and each represent a hydrogen atom, a halogen atom, a nitro group, a nitrile group, or a trifluoromethyl group; $R_4$ represents a substituted or unsubstituted acyloxymethyl group, an alkoxycarbonyloxymethyl group, a (2-oxo-1,3-dioxolen-4-yl)methyl group, a (5-substituted-2-oxo-1,3-dioxolen-4-yl)methyl group, or an acyl group; $R_5$ represents a lower alkyl group or a substituted alkyl group; and $R_6$ represents a hydrogen atom, a lower alkoxymethyl group, or a lower acyloxymethyl group, is disclosed. The compound is stereospecifically hydrolyzed by the action of an enzyme to provide an optically active 1,4-dihydro-3-pyridinemonocarboxylic acid which is useful as an intermediate of pharmaceuticals in good optical purity and yield.

5 Claims, No Drawings

PROCESS FOR PREPARING 1,4 DIHYDROPYRIDINE COMPOUNDS

FILED OF THE INVENTION

This invention relates to an optically active 1,4-dihydropyridinemonocarboxylic acid which is an important intermediate of pharmaceuticals and a process for preparing the same by asymmetric synthesis utilizing stereoselectivity of an enzyme.

BACKGROUND OF THE INVENTION

Optical resolution for preparing optically active -1,4-dihydropyridine derivatives has been reported in *Chem. Pharm. Bull.*, Vol. 37, p. 2225 (1989) and *J. Med. Chem.*, Vol. 29, p. 2504 (1986). These known techniques, however, did not succeed to selectively obtain either only one of optical isomers as desired and are not therefore regarded industrially advantageous. Under the present situation, most of pharmaceuticals having a 1,4-dihydropyridine skeleton with an asymmetric carbon atom have been developed and put into medical use in the form of a racemate. A solution to this problem has thus been keenly demanded.

SUMMARY OF THE INVENTION

An object of the present invention is to provide a novel prochiral 1,4-dihydropyridine compound which is suited to asymmetric hydrolysis with an enzyme catalyst.

Another object of the present invention is to provide a process for asymmetrically synthesizing a desired optically active compound useful as an intermediate for pharmaceuticals.

The inventors have made extensive researches for a 1,4-dihydropyridine compound which is suitable as a substrate of asymmetric synthesis using a hydrolase as a catalyst. As a result, they have found that a novel prochiral 1,4-dihydropyridine derivative represented by formula (I):

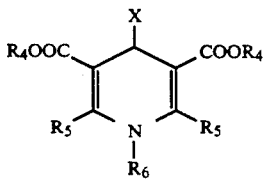
(I)

wherein X represents an alkyl group, or a group of

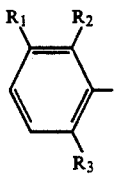

in which $R_1$, $R_2$, and $R_3$ may be the same or different and each represent a hydrogen atom, a halogen atom, a nitro group, a nitrile group, or a trifluoromethyl group; $R_4$ represents a substituted or unsubstituted acyloxymethyl group, an alkoxycarbonyloxymethyl group, a (2-oxo-1,3-dioxolen-4-yl)methyl group, a (5-substituted-2-oxo-1,3-dioxolen-4-yl) methyl group, or an acyl group; $R_5$ represents a lower alkyl group or a substituted alkyl group; and $R_6$ represents a hydrogen atom, a lower alkoxymethyl group, or a lower acyloxymethyl group, is stereospecifically hydrolyzed by the action of an enzyme catalyst to produce a novel optically active 1,4-dihydro-pyridinemonocarboxylic acid derivative represented by formula (II):

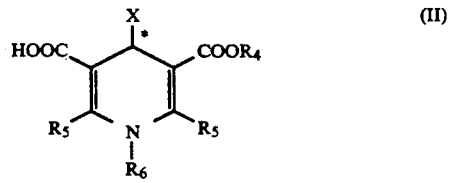
(II)

wherein X, $R_4$, $R_5$, and $R_6$ are as defined above; and * indicates an optically active site, with a satisfactory optical yield and a satisfactory reaction yield.

DETAILED DESCRIPTION OF THE INVENTION

In formulae (I) and (II), X represents an alkyl group, or a group of

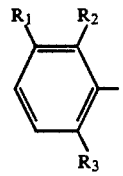

in which $R_1$, $R_2$, and $R_3$ may be the same or different and each represent a hydrogen atom, a halogen atom, a nitro group, a nitrile group, or a trifluoromethyl group; $R_4$ represents a substituted or unsubstituted acyloxymethyl group (e.g., pivaloyloxymethyl, 1-acetoxyethyl), an alkoxycarbonyloxymethyl group (e.g., 1-(ethoxycarbonyloxy)ethyl), a (2-oxo-1,3-dioxolen-4-yl)methyl group, a (5-substituted -2-oxo-1,3-dioxolen-4-yl)methyl group (the substituent includes methyl and ethyl groups), or an acyl group (e.g., pivaloyl); $R_5$ represents a lower alkyl group (e.g., methyl, ethyl) or a substituted alkyl group (the substituent includes fluorine, chlorine, lower alkoxy); and $R_6$ represents a hydrogen atom, a lower alkoxymethyl group (e.g., methoxymethyl, ethoxymethyl), or a lower acyloxymethyl group (e.g., pivaloyloxymethyl).

The enzyme which can be used as a catalyst in the present invention is not limited as long as capable of catalyzing the reaction of the prochiral 1,4-dihydropyridine derivative of formula (I) to produce the optically active 1,4-dihydropyridinemonocarboxylic acid derivative of formula (II). Specific examples of such an enzyme include lipase originated from microorganisms belonging to the genus Pseudomonas, and more specifically *Pseudomonas cepacia*, *Pseudomonas fraqi*, etc. These lipase species are commercially available, for example, under trade names of Lipase PS (product of Amano Pharmaceutical Co., Ltd.) and Lipase B (product of Sapporo Breweries Ltd.). Enzymes to be used may be either crude or purified. Microbial cells capable of producing these enzymes are also employable.

The reaction is usually carried out at a temperature of from 0° to 40° C. for a period of from 1 to 120 hours preferably in such a manner that the enzyme be dispersed throughout the reaction system. The lipase may be used either as it is or as immobilized on an appropriate carrier.

The reaction is usually performed in an organic solvent containing water. The organic solvent is not particularly limited and includes, for example, diethyl ether, isopropyl ether, ethanol, methanol, acetone, benzene, and chloroform. After the reaction, the enzyme can be removed easily in a usual manner, for example, by filtration through filter paper. The reaction product, if containing much water, can be isolated by extraction with chloroform, benzene, diethyl ether, etc. If desired, the reaction product can easily be purified by, for example, silica gel column chromatography.

Enzymatic hydrolysis of the prochiral 1,4-dihydropyridine derivative of formula (I) gives the optically active 1,4-dihydropyridinemonocarboxylic acid derivative of formula (II), an important intermediate of pharmaceuticals, with extremely excellent results in both optical yield and reaction yield which are of great advantage in industrial scale production. That is, the present invention establishes a novel technique for producing a number of 1,4-dihydropyridine compounds useful as pharmaceuticals in the form of an optically active isomer which have been developed and put into medical use in the form of their racemate.

The present invention is now illustrated in greater detail with reference to Examples, but it should be understood that the present invention is not deemed to be limited thereto. All the percents are by weight unless otherwise indicated. All the ratios of developing solvents in column chromatography, high performance liquid chromatography, and thin layer chromatography are by volume unless otherwise indicated.

EXAMPLE 1

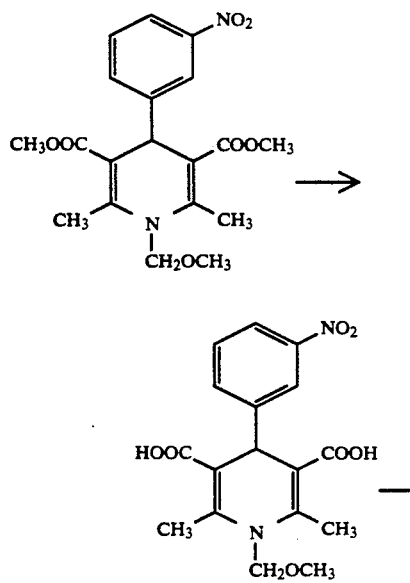

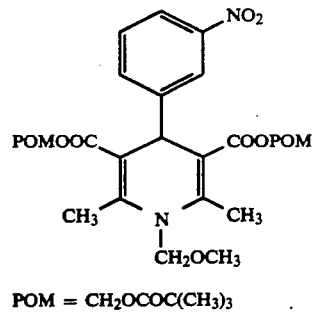

POM = CH₂OCOC(CH₃)₃

1) In methanol were dissolved 14.0 g of potassium hydroxide and 3.6 g of benzyltributylammonium bromide, and 19.5 g of dimethyl 1,4-dihydro-2,6-dimethyl-1-methoxymethyl-4-(3-nitrophenyl)-3,5-pyridinecarboxylate was added to the solution, followed by refluxing for 48 hours. To the reaction mixture was added 20 m; of water, and the mixture was made acidic (pH=1-2). The thus formed reddish brown precipitate was collected by filtration, washed with cold ethanol, and dried to obtain 15.9 g of crude 1,4-dihydro-2,6-dimethyl-1-methoxymethyl-4-(3-nitrophenyl)-3,5-pyridinedicarboxylic acid.

IR (nujol): 1685 cm⁻¹

2) In 40 m; of dimethylformamide was dissolved 8.0 g of the resulting reddish brown powder, and 9.7 g of diisopropylethylamine and 9.0 g of chloromethyl pivalate were added thereto in an argon stream, followed by stirring for 48 hours. The reaction mixture was extracted with dichloromethane. The separated dichloromethane layer was washed successively with water and a saturated sodium chloride aqueous solution, and dried over anhydrous magnesium sulfate. Magnesium sulfate was removed by filtration, and the filtrate was concentrated under reduced pressure. The residue was purified by silica gel column chromatography (ethyl acetate/hexane=1/4) to obtain 6.3 g (yield: 43%) of bis(-pivaloyloxymethyl) 1,4-dihydro-2,6-dimethyl-1-methoxymethyl-4-(3-nitrophenyl)-3,5-pyridinedicarboxylate as a pale yellow crystal.

Melting point: 73°-74° C. (ethanol/n-hexane) IR (nujol): 1745, 1715 cm⁻¹

¹H-NMR (CDCl₃) δ: 1.11 (18H, s, 6×CH₃), 2.54 (6H, s, 2×CH₃), 3.30 (3H, s, OCH₃), 4.82 (2H, s, NCH₂O), 5.18 (1H, s, >CH—), 5.79 (2H, d, J=5.5Hz, OCH$_A$H$_B$O), 5.85 (2H, d, J=5.5Hz, OCH$_A$H$_B$O), 7.32-7.33, 7.62-7.69, 7.85-8.00 (4H, m, C₆H₄)

¹³C-NMR (CDCl₃) δ: 16.30 (2×C), 26.77 (6×C), 38.43 (2×C), 38.68, 55.09, 77.15, 79.45 (2×C), 106.73 (2×C), 121.60, 122.11, 128.93, 134.28, 147.29, 148.53, 150.90 (2×C), 165.43 (2×C), 177.05 (2×C)

EXAMPLE 2

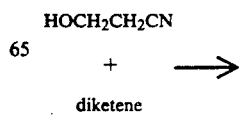

diketene

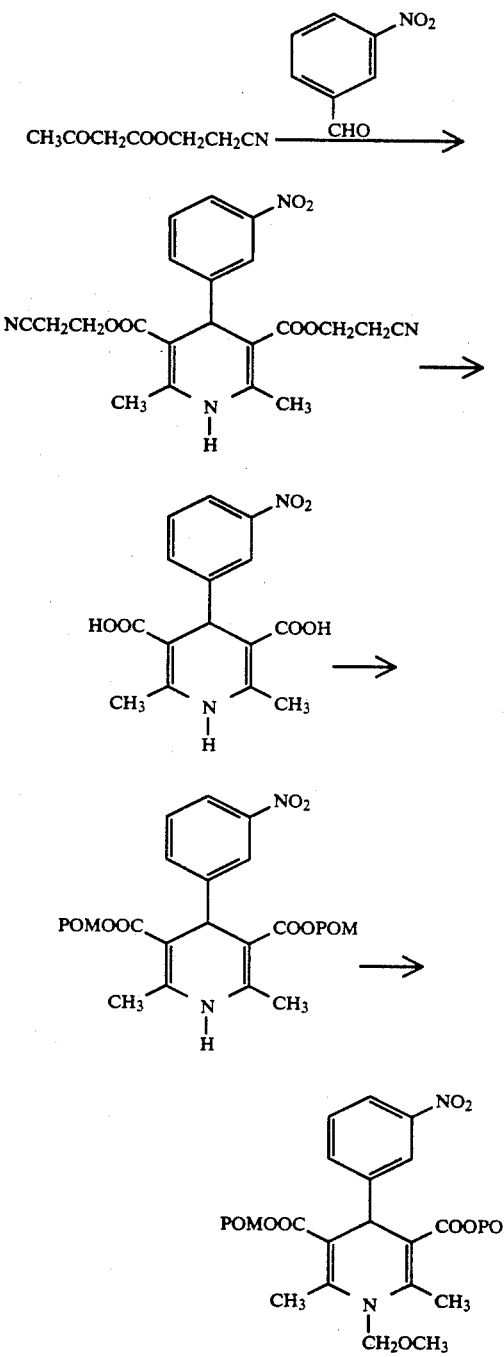

1) In 5.0 g of ethylene cyanohydrin was dissolved 29 mg of dimethylaminopyridine, and 5.9 g of diketene was added thereto dropwise at 70° to 80° C., followed by stirring at 70° to 80° C. for 2 hours. Ten grams of the resulting cyanoethyl acetoacetate and 4.0 g of m-nitrobenzaldehyde were dissolved in 13 ml of a 7% ammonia/methanol solution, and the solution was stirred in a closed tube at 90° C. for 8 hours. After the reaction, the reaction mixture was freed of the solvent by distillation, and the residue was purified by silica gel column chromatography (methanol/dichloromethane=1/50). Recrystallization from ethanol gave 5.0 g (yield: 44%) of dicyanoethyl 1,4-dihydro-2,6-dimethyl-4-(3-nitrophenyl)-3,5-pyridinedicarboxylate as a yellow needle-like crystal.

Melting point: 161°–162° C. (ethanol)
IR (nujol): 3320, 2250, 1680 cm$^{-1}$
$^1$H-NMR (CDCl$_3$) δ:2.40 (6H, s, 2×CH$_3$), 2.69 (4H, t, J=6.4Hz, 2×OCH$_2$), 4.28 (4H, t, J=6.4Hz, 2×CH$_2$CN), 5.13 (1H, s, >CH—), 6.19 (1H, s, NH), 7.40–7.46, 7.70–7.73, 8.00–8.12 (4H, m, C$_6$H$_4$)
$^{13}$C-NMR (CDCl$_3$) δ: 18.12 (2×C), 19.76 (2×C), 39.54, 58.49 (2×C), 102.51 (2×C), 117.12 (2×C), 121.74, 122.82, 129.12, 134.42, 146.37, 148.49, 149.13 (2×C), 166.05 (2×C)

2) In 30 ml of acetone containing 60 ml of 1N sodium hydroxide was dissolved 4.3 g of the dicyanoethyl 1,4-dihydro-4-(3-nitrophenyl)-2,6-dimethyl -3,5-pyridinedicarboxylate obtained in (1) above, and the solution was stirred for 3 hours. After the reaction, the reaction mixture was diluted with 60 ml of water and washed twice with dichloromethane. The separated aqueous layer was rendered acidic (pH=1–2) with concentrated hydrochloric acid under ice-cooling and stirred for 3 hours. The thus formed crystal was collected by filtration, washed with diethyl ether, and dried under reduced pressure to obtain 2.9 g (yield: 91%) of 1,4-dihydro -2,6-dimethyl-4-(3-nitrophenyl)-3,5-pyridinedicarboxylic acid as a yellow powder.

Melting point: 179°–180° C. (methanol/n-hexane)
IR (nujol): 3360, 1680 cm$^{-1}$
$^1$H-NMR (CD$_3$OD) δ: 2.34 (6H, s, 2×CH$_3$), 4.86 (1H, s, >CH—), 5.10 (1H, s, NH), 7.40–7.46, 7.65–7.66, 7.68–8.11, 8.11–8.12 (4H, m, C$_6$H$_4$)
$^{13}$C-NMR (CD$_3$OD) δ: 18.75 (2×C), 41.20, 103.28 (2×C), 121.98, 123.54, 130.03, 135.32, 148.09, 149.50, 151.68 (2×C), 171.24 (2×C)

3) In dimethylformamide was dissolved 1.6 g of the 1,4-dihydro-2,6-dimethyl-4-(3-nitrophenyl) -3,5-pyridinedicarboxylic acid obtained in (2) above, and 0.6 g of 60% oily sodium hydride was added thereto under ice-cooling with stirring in an argon stream. Thirty minutes later, 1.8 g of chloromethyl pivalate was slowly added thereto dropwise under cooling with ice, followed by stirring at room temperature for 18 hours. After completion of the reaction, 5 ml of acetic acid was added to the reaction mixture, and the mixture was diluted with dichloromethane, washed successively with water and a saturated sodium chloride aqueous solution, and dried over anhydrous magnesium sulfate. Magnesium sulfate was removed by filtration, and the filtrate was concentrated under reduced pressure. The residue was purified by silica gel column chromatography (ethyl acetate/hexane=1/4) to obtain 1.2 g (yield: 46%) of bis(pivaloyloxymethyl) 1,4-dihydro-2,6-dimethyl-4-(3-nitrophenyl) -3,5-pyridinedicarboxylate as a yellow crystal.

Melting point: 124°–125° C. (ethanol)
IR (nujol): 3340, 1750, 1720 cm$^{-1}$
$^1$H-NMR (CDCl$_3$) δ: 1.10 (18H, s, 6×CH$_3$), 2.37 (6H, s, 2×CH$_3$), 5.07 (1H, s, >CH—), 5.53 (2H, d, J=5.8Hz, OCH$_A$H$_B$O), 5.72 (2H, d, J=5.8Hz, OCH$_A$H$_B$)), 6.00 (1H, s, NH), 7.26–7.39, 7.43–7.67, 7.97–8.06 (4H, m, C$_6$H$_4$)
$^{13}$C-NMR (CDCl$_3$) δ: 19.98 (2×C), 26.75 (6×C), 38.65 (2×C), 39.36, 79.15 (2×C), 102.69 (2×C), 121.53, 122.80, 128.68, 134.73, 146.32, 148.50, 149.00 (2×C), 165.25 (2×C), 177.09 (2×C)

4) In dried tetrahydrofuran was dissolved 546 mg of the bis(pivaloyloxymethyl) 1,4-dihydro-2,6-dimethyl-4-(3-nitrophenyl)-3,5-pyridinedicarboxylate obtained in (3) above, and 80 mg of 60% oily sodium hydride was added to the solution under ice-cooling with stirring in an argon stream, followed by stirring for 1 hour. Then, 120 mg of chloromethyl ether was added thereto dropwise under ice-cooling, followed by stirring at room temperature for 18 hours. To the reaction mixture was added 0.5 ml of acetic acid, and tetrahydrofuran was removed by distillation. The residue was diluted with ethyl acetate, washed successively with water and a saturated sodium chloride aqueous solution, and dried over anhydrous magnesium sulfate. Magnesium sulfate was removed by filtration, and the filtrate was concentrated under reduced pressure. The residue was purified by silica gel column chromatography (ethyl acetate/hexane=¼) to obtain 200 mg (yield: 34%) of bis(-pivaloyloxymethyl) 1,4-dihydro-2,6-dimethyl-1-methoxymethyl-4-(3-nitrophenyl) -3,5-pyridinedicarboxylate as a pale yellow crystal.

The melting point and various spectral data of the product were in complete agreement with those of the product of Example 1.

EXAMPLE 3

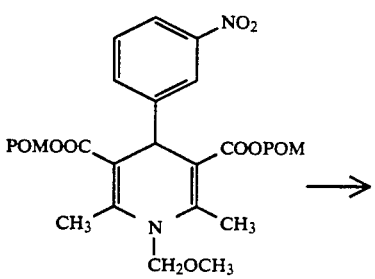

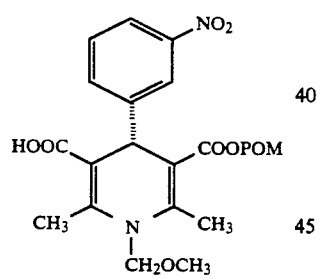

In 20 ml of isopropyl ether saturated with water was dissolved 1.2 g of bis(pivaloyloxymethyl) 1,4-dihydro-2,6-dimethyl-1-methoxymethyl-4-(3-nitrophenyl) -3,5-pyridinedicarboxylate obtained in Example 1 or 2 as a substrate. To the substrate solution was added 300 mg of Lipase B, and the reaction system was stirred at room temperature for 3 hours. Any insoluble matter was removed by filtration and washed with dichloromethane. The filtrate was concentrated under reduced pressure, and the residue was subjected to silica gel column chromatography (ethyl acetate/hexane=¼) to obtain 0.9 g (yield: 95%) of (S)-1,4-dihydro-2,6-dimethyl-1-methoxymethyl-4-(3-nitrophenyl)-5-pivaloyloxymethoxycarbonyl-3-pyridinecarboxylic acid as a colorless crystal.

Melting point: 84°-85° C. (ethyl acetate/n-hexane)
[α]$_D$: +42.6° (c=1.0, acetone)
IR (nujol): 1710, 1690 cm$^{-1}$
$^1$H-NMR (CDCl$_3$) δ: 1.12 (9H, s, 3×CH$_3$), 2.55 (3H, s, CH$_3$),
2.57 (3H, s, CH$_3$), 3.33 (3H, s, OCH$_3$),
4.81 (2H, s, NCH$_2$O), 5.19 (1H, s, >CH—), 5.77 (1H, d, J=5.3Hz, OCH$_A$H$_B$O), 5.83 (1, d, J=5.3Hz, OCH$_A$H$_B$O), 7.62–7.65, 7.98–8.00 (4H, m, C$_6$H$_4$)

$^{13}$C-NMR (CDCl$_3$) δ: 16.25, 16.35, 26.77 (3×C), 38.21, 38.69, 55.08, 77.16, 79.38, 106.74, 106.80, 121.61, 122.04, 128.99, 134.25, 147.19, 148.47, 151.10, 151.57, 165.43, 172.51, 177.15

EXAMPLE 4

In 20 ml of a phosphoric acid buffer solution (pH=8) containing 2 ml of acetone was suspended 590 mg of the same substrate as used in Example 3, and 300 mg of Lipase B was added thereto, followed by stirring at room temperature for 24 hours. The reaction mixture was extracted three times with 20 ml portions of dichloromethane, and the extract was dried over anhydrous magnesium sulfate, followed by concentration. The residue was subjected to silica gel column chromatography (ethyl acetate/hexane=¼) to obtain 380 g (yield: 80%) of a colorless crystal. The specific rotation, melting point and various spectral data of the product were in entire agreement with those of the product obtained in Example 3.

TEST EXAMPLE 1

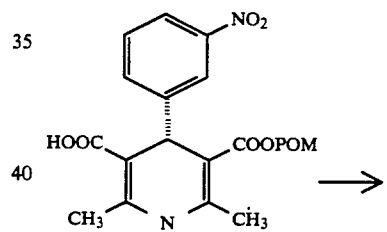

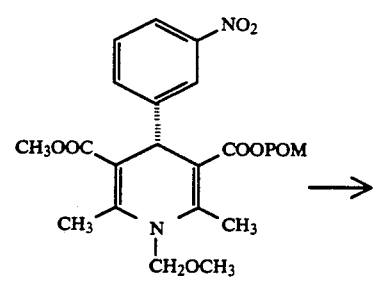

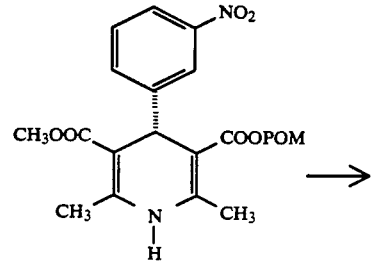

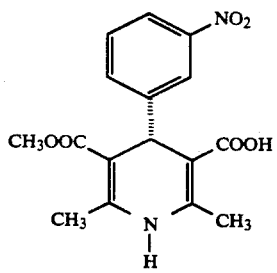

1) In 2 ml of dichloromethane was dissolved 476 mg of (S)-1,4-dihydro-2,6-dimethyl-1-methoxymethyl-4-(3-nitrophenyl)-5-pivaloyloxymethoxycarbonyl-3-pyridinecarboxylic acid obtained in Example 3 ro 4, and 6 ml of a 0.5M solution of diazomethane in diethyl ether was added to the solution under cooling with ice, followed by stirring for 1 hour. Acetic acid was added to the reaction mixture until the yellow color disappeared, and the reaction mixture was concentrated. The residue was purified by short silica gel column chromatogrpahy (ether acetate/hexane=¼) to give 460 mg (yield: 94%) of (S)-methyl pivaloyloxymethyl 1,4-dihydro -2,6-dimethyl-1-methoxymethyl-4-(3-nitrophenyl) -3,5-pyridinedicarboxylate as a pale yellow crystal.

Melting point: 113°–114° C. (ethyl acetate/n-hexane)
$[\alpha]_D$: +22.0° (c=1.2, acetone)
IR (nujol): 1750, 1710 cm$^{-1}$
$^1$H-NMR (CDCl$_3$) δ: 1.13 (9H, s, 3×CH$_3$), 2.54 (6H, s, 2×CH$_3$), 3.33 (3H, s, OCH$_3$), 3.70 (3H, s, COOCH$_3$), 4.81 (2H, s, NCH$_2$O), 5.16 (1H, s, >CH—), 5.78 (1H, d, J=5.3Hz, OCH$_A$H$_B$O), 5.83 (1H, d, J=5.3Hz, OCH$_A$H$_B$O), 7.33–7.39, 7.56–7.96, 7.98–8.01 (4H, m, C$_6$H$_4$)
$^{13}$C-NMR (CDCl$_3$) δ: 28.46, 28.75, 26.77 (3×C), 38.53, 38.68, 51.55, 55.03, 77.10, 79.28, 106.10, 107.84, 121.53, 122.16, 128.93, 133.93, 147.51, 148.47, 148.99, 151.36, 165.57, 167.48, 177.15

An aliquot of the product (non-recrystallized) was treated with a potassium hydroxide solution in methanol solution to obtain (R)-1,4-dihydro-2,6-dimethyl-5-methoxycarbonyl-1-methoxymethyl-4-(3-nitrophenyl)-3-pyridinecarboxylic acid, which was then reacted with phenyldiazomethane to obtain (S)-benzyl methyl 1,4-dihydro -2,6-dimethyl-1-methoxymethyl-4-(3-nitrophenyl) -3,5-pyridinedicarboxylate. Optical purity of the product was found to be higher than 99% ee by high performance liquid chromatography (HPLC) (isopropyl alcohol/hexane=1/10) using "CHIRALCEL OD".

Melting point: 69°–70° C. (isopropyl ether/n-hexane)
IR (nujol): 1705, 1680 cm$^{-1}$
$^1$H-NMR (CDCl$_3$) δ: 2.53 (3H, s, CH$_3$), 2.54 (3H, s, CH$_3$), 3.32 (3H, s, OCH$_3$), 3.69 (3H, s, COOCH$_3$), 4.80 (2H, s, NCH$_2$O), 5.09 (1H, d, J=12.5Hz, OCH$_A$H$_B$O), 5.19 (1H, s, >CH—), 5.22 (1H, d, J=12.5Hz, OCH$_A$H$_B$O), 7.23–7.32, 7.47–7.50, 7.97–8.01 (9H, m, C$_6$H$_4$ and C$_6$H$_5$)
$^{13}$C-NMR (CDCl$_3$) δ: 16.12, 16.20, 38.95, 51.49, 55.01, 77.06, 107.28, 107.49, 121.44, 122.35, 127.77, 128.11, 128.14, 128.20, 128.49, 128.86, 133.94, 136.10, 147.82, 148.37, 149.07, 149.61, 167.01, 167.68

To 5 ml of acetone containing 1 ml of 2N hydrochloric acid was added 390 mg of the (S)-methyl pivaloyloxymethyl 1,4-dihydro-2,6-dimethyl-1-methoxymethyl-4-(3-nitrophenyl) -3,5-pyridinedicarboxylate obtained in (1) above, and the mixture was stirred at 25° C. for 2 hours. To the reaction mixture was added dropwise 2 ml of a 1N sodium hydroxide aqueous solution under ice-cooling, followed by concentration under reduced pressure. The residue was extracted twice with 10 ml portions of dichloromethane, and the extract was dried over anhydrous magnesium sulfate and concentrated. The residue was subjected to short silica gel column chromatography (ethyl acetate/hexane=¼) to obtain 350 mg (yield: 98%) of (S)-methyl pivaloyloxymethyl 1,4-dihydro-2,6-dimethyl-4-(3-nitrophenyl) -3,5-pyridinedicarboxylate as a pale yellow viscous oily substance.

$[\alpha]_D$: +10.3° (c=1.3, acetone)
IR (nujol): 3340, 1750, 1710 cm$^{-1}$
$^1$H-NMR (CDCl$_3$) δ: 4.84 (9H, s, 3×CH$_3$), 2.37 (6H, s, 2×CH$_3$), 3.64 (3H, s, OCH$_3$), 5.09 (1H, s, >CH—), 5.73 (1H, d, J=5.3Hz, OCH$_A$H$_B$O), 5.76 (1H, d, J=5.3Hz, OCH$_A$H$_B$O), 6.19 (1H, s, NH), 7.34–7.40, 7.62–7.66, 8.00–8 08 (4H, m, C$_6$H$_4$)
$^{13}$C-NMR (CDCl$_3$) δ: 19.45, 19.91, 26.74 (3×C), 38.64, 39.46, 51.20, 78.99, 101.90, 103.68, 121.46, 122.78, 128.70, 134.44, 144.71, 147.05, 148.41, 149.36, 165.46, 167.39, 177.21

To a solution of 0.5 g of potassium hydroxide in 5 ml of methanol was added 223 mg of the (S)-methyl pivaloyloxymethyl 1,4-dihydro-2,6-dimethyl-4-(3-nitrophenyl) -3,5-pyridinedicarboxylate obtained in (2) above, and the mixture was stirred for 2 hours. To the mixture was added 1 ml of 6N hydrochloric acid under cooling with ice, followed by concentration under reduced pressure. The residue was extracted twice with 10 m; portions of ethyl acetate, and the extract was dried over anhydrous magnesium sulfate and concentrated to obtain 153 mg (yield: 92%) of (R)-1,4-dihydro-2,6-dimethyl-4-(3-nitrophenyl)-5-methoxycarbonyl-3-pyridinecarboxylic acid as a pale yellow crystal.

Melting point: 187°–188° C. (ethyl acetate/n-hexane)
$[\alpha]_D$: −19.5° (c=0.8, acetone) (data in the literature: $[\alpha]_D$= −19.6° (c=0.542, acetone), refer to M. Kajino, Y Wada, Y. Magai, A. Nagaoka, and K. Meguro, Chem. Pharm. Bull., Vol. 37, p. 2225 (1989))
IR (nujol): 3350, 1680, 1660 cm$^{-1}$
$^1$H-NMR (CD$_3$OD) δ: 2.33 (6H, s, 2×CH$_3$), 3.62 (3H, s, OCH$_3$), 4.55 (1H, s, NH), 5.08 (1H, s, >CH—), 7.42–7.45, 7.64–7.65, 7.97–8.09 (4H, m, C$_6$H$_4$)
$^{13}$C-NMR (CD$_3$OD) δ: 18.69 (2×C), 40.97, 51.44, 102.77, 103.58, 122.01, 123.58, 130.02, 135.16, 147.70, 148,31, 149.47, 151,56, 169.67, 173.33

EXAMPLE 5

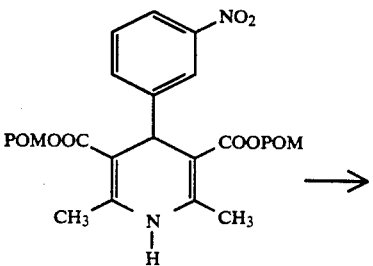

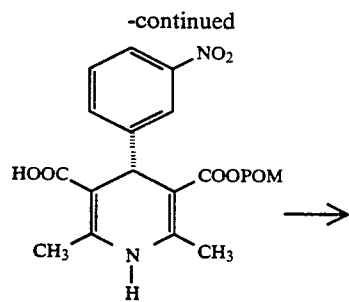

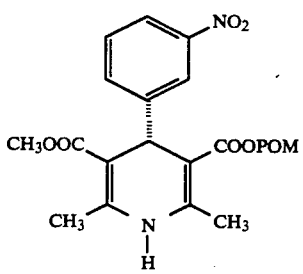

1) In 20 ml of isopropyl ether saturated with water was dissolved 546 mg of bis(pivaloyloxymethyl) 1,4-dihydro-2,6-dimethyl-4-(3-nitrophenyl)-3,5-pyridinedicarboxylate obtained in Example 2-(3), and 200 mg of Lipase B was added thereto, followed by stirring at room temeprature for 35 hours. Any insoluble matter was removed by filtration and washed with dichloromethane, and the filtrate was concentrated under reduced pressure. The resulting residue was purified by short silica gel column chromatography (ethyl acetate/hexane=$\frac{1}{4}$) to obtain 35 mg (yield: 83%) of (S)-1,4-dihydro 2,6-dimethyl-4-(3-nitrophenyl)-5-pivaloyloxymethoxycarbonyl-3-pyridinecarboxylic acid as a pale yellow crystal.

Melting point: 146°–148° C. (ethyl acetate/n-hexane)
$[\alpha]_D$: +27.9° (c=0.8, acetone)
IR (nujol): 3340, 1750, 1690 cm$^{-1}$ $^1$H-NMR (CDCl$_3$) δ: 1.10 (9H, s, 3×CH$_3$), 2.38 (6H, s, 2×CH$_3$), 5.09 (1H, s, >CH—), 5.72 (1H, d, J=5.3Hz, OCH$_A$H$_B$O), 5.76 (1H, d, J=5 3Hz, OCH$_A$H$_B$O), 6.04 (1H, s, NH), 7.33–7.39, 7.66–7.69, 7.96–8.07 (4H, m, C$_6$H$_4$)

$^{13}$C-NMR (CDCl$_3$) δ: 19.89, 20.04, 26.74 (3×C), 38.65, 39.19, 79.05, 102.63, 102.84, 121.55, 122.77, 128.73, 134.69, 146.53, 146.77, 148.42, 148.94, 165.29, 172.21, 177.18

The carboxylic acid prepared in (1) above was treated with a diethyl ether solution of diazomethane. The resulting (S)-methyl pivaloyloxymethyl 1,4-dihydro-2,6-dimethyl-4-(3-nitrophenyl)-3,5-pyridinedicarboxylate had a specific rotation $[\alpha]_D$ of +9.6° (c=0.6, acetone) (93% ee).

EXAMPLE 6

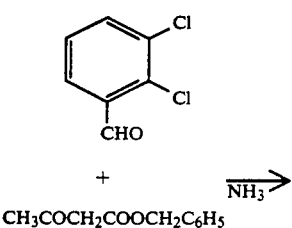
+ CH$_3$COCH$_2$COOCH$_2$C$_6$H$_5$ $\xrightarrow{NH_3}$

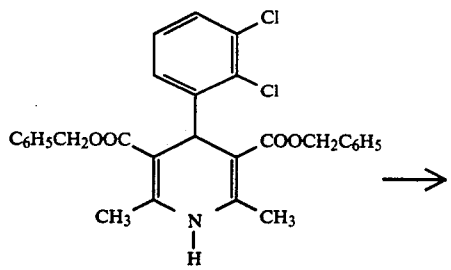

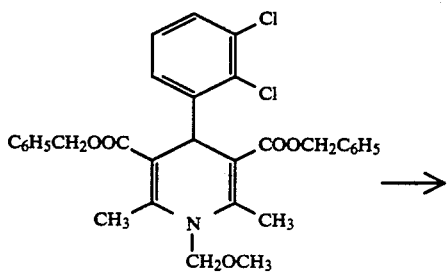

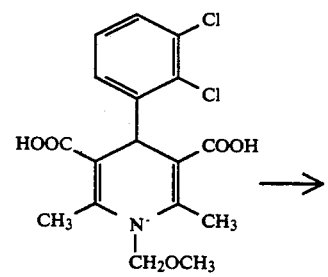

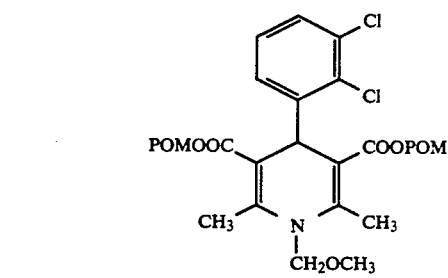

In a 7% ammonia solution in methanol were dissolved 2.6 g of 2,3-dichlorobenzaldehyde and 5.8 g of benzyl acetoacetate, and the solution was stirred in a closed tube at 90° C. for 10 hours, followed by concentration under reduced pressure. The residue was purified by silica gel column chromatography (ethyl acetate/hexane=$\frac{1}{4}$) to obtain 4.8 g (yield: 30%) of dibenzyl 4-(2,3-dichlorophenyl)-1,4-dihydro-2,6-dimethyl-3,5-pyridinedicarboxylate as a yellow crystal.

Melting point: 131°–132° C. (ethanol/n-hexane)
IR (nujol): 3310, 1700 cm$^{-1}$ $^1$H-NMR (CDCl$_3$) δ: 2.26 (6H, s, 2×CH$_3$), 5.05 (4H, s, 2×CH$_2$Ph), 5.50 (1H, s, >CH—), 5.79 (1H, s, NH), 6.91–6.97, 7.14–7.27 (13H, m, C$_6$H$_3$ and 2×C$_6$H$_5$)

$^{13}$C-NMR (CDCl$_3$) δ: 19.64 (2×C), 39.06, 65.55 (2×C), 103.17 (2×C), 126.84 (2×C), 127.80, 128.12, 128.15 (4×C), 128.31, 130.09 (4×C), 131.36, 132.95, 136.45 (2×C), 144.61, 147.54 (2×C), 167.06 (2×C)

2) In 50 ml of dried tetrahydrofuran was dissolved 4.0 g of the dibenzyl 4-(2,3-dichlorophenyl) -1,4-dihydro- 2,6-dimethyl-3,5-pyridinedicarboxylate obtained in (1) above in an argon stream, and 840 mg of 60% oily sodium hydride was slowly added thereto under cooling with ice. After stirring for 10 minutes, 845 mg of chloromethyl ether was added thereto dropwise, followed by stirring at 0° C for 3 hours. To the reaction mixture was added 2 ml of acetic acid, followed by concentration under reduced pressure. The residue was diluted with ethyl acetate, washed successively with water, a saturated sodium hydrogencarbonate aqueous solution, and a saturated sodium chloride aqueous solution, and dried over anhydrous sodium sulfate. After sodium sulfate was removed by filtration, the filtrate was concentrated under reduced pressure, and the residue was subjected to silica gel column chromatography (ethyl acetate/hexane=3/7) to obtain 3.2 g (yield: 81%) of dibenzyl 4-(2,3-dichlorophenyl) -1,4-dihydro-2,6-dimethyl-1-methoxymethyl-3,5-pyridinedicarboxylate as a colorless crystal.

Melting point: 116°-117° C. (ethanol/n-hexane)
IR (nujol): 1700 cm$^{-1}$ $^1$H-NMR (CDCl$_3$) δ: 2.43 (6H, s, 2×CH$_3$), 3.32 (3H, s, OCH$_3$), 4.76 (2H, s, NCH$_2$O), 5.06 (2H, d, J=12.7Hz, OCH$_A$H$_B$O), 5.13 (2H, d, J=12.7Hz, OCH$_A$H$_B$O), 6.92-6.98, 7.06-7.08, 7.17-7.27 (13H, m, C$_6$H$_3$ and 2×C$_6$H$_5$)

$^{13}$C-NMR (CDCl$_3$) δ: 16.01 (2×C), 38.61, 54.90, 65.96 (2×C), 77.04, 107.43 (2×C), 127.13, 127.85 (2×C), 128.06 (4×C), 128.35 (4×C), 128.43, 128.69, 131.03, 133.06, 136.24 (2×C), 145.83, 147.43 (2×C), 167.47 (2×C)

3) In a mixture of 60 ml of methanol and 40 ml of acetone was dissolved 3.4 g of the dibenzyl 4-(2,3-dichlorophenyl)-1,4-dihydro-2,6-dimethyl-1-methoxymethyl-3,5-pyridinedicarboxylate obtained in (2) above, and the solution was subjected to catalytic reduction using 150 mg of palladium-on-carbon as a catalyst in a hydrogen stream. The catalyst was removed by filtration, and the filtrate was concentrated under reduced pressure. The resulting crystal was recrystallized from methanol/hexane to obtain 1.39 g (yield: 60%) of 4-(2,3-dichlorophenyl) -1,4-dihydro-2,6-dimethyl-1-methoxymethyl -3,5-pyridinedicarboxylic acid as a colorless crystal.

Melting point: 155°-156° C. (ethanol/n-hexane)
IR (nujol): 1690 cm$^{-1}$ $^1$H-NMR (CDCl$_3$) δ: 2.44 (6H, s, 2×CH$_3$), 3.35 (3H, s, OCH$_3$), 4.87 (2H, s, NCH$_2$O), 5.51 (1H, s, >CH—), 7.08-7.31 (3H, m, C$_6$H$_3$)

$^{13}$C-NMR (CDCl$_3$) δ: 16.17 (2×C), 40.32, 55.07, 78.17, 108.76 (2×C), 128.32, 128.49, 128.84, 129.48, 129.82, 133.91, 147.54, 148.49 (2×C), 171.79 (2×C)

4) In 10 ml of dimethylformamide was dissolved 740 mg of the 4-(2,3-dichlorophenyl)-1,4-dihydro-2,6-dimethyl-1-methoxymethyl-3,5-pyridinedicarboxylic acid prepard in (3) above, and 240 mg of 60% oily sodium hydride was added thereto at 0° C. in an argon stream with stirring. After stirring at room temperature for 30 minutes, 900 mg of chloromethyl pivalate was added thereto dropwise under cooling with ice, followed by stirring for 18 hours. The reaction mixture was neutralized with acetic acid, diluted with dichloromethane, washed successively with water and a saturated sodium chloride aqueous solution, and dried over anhydrous sodium sulfate. Sodium sulfate was removed by filtration, and the filtrate was concentrated under reduced pressure. The residue was purified by silica gel column chromatography (ethyl acetate/hexane=½) to obtain 1.1 g (yield: 90%) of bis(pivaloyloxymethyl) 4-(2,3-dichlorophenyl)-1,4-dihydro-2,6-dimethyl-1-methoxymethyl-3,5-pyridinedicarboxylate as a colorless crystal.

Melting point: 103°-104° C. (ethyl acetate/n-hexane)
IR (nujol): 1750, 1710 cm$^{-1}$ $^1$H-NMR (CDCl$_3$) δ: 1.12 (18H, s, 6×CH$_3$), 2.46 (6H, s, 2×CH$_3$), 3.37 (3H, s, OCH$_3$), 4.71 (2H, s, NCH$_2$O), 5.52 (1H, s, >CH—), 5.74 (2H, d, J=5.6Hz, OCH$_A$H$_B$O), 5.78 (2H, d, J=5.6Hz, OCH$_A$H$_B$O), 7.00-7.06, 7.11-7.14, 7.23-7.27 (3H, m, C$_6$H$_3$)

$^{13}$C-NMR (CDCl$_3$) δ: 16.21 (2×C), 26.80 (2×C), 38.23, 38.64 (2×C), 54.93, 77.26, 79.50 (2×C), 106.59 (2×C), 127.14, 128.67, 128.95, 131.19, 133.26, 145.27, 149.13 (2×C), 166.02 (2×C), 176.96 (2×C)

EXAMPLE 7

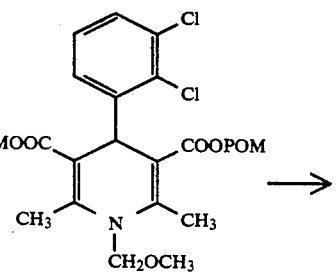

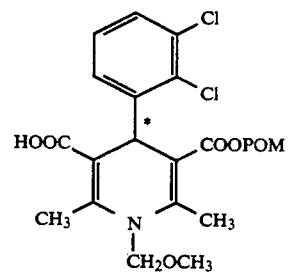

In 15 ml of isopropyl ether saturated with water was dissolved 614 mg of bis(pivaloyloxymethyl) 4-(2,3-dichlorophenyl)-1,4-dihydro-2,6-dimethyl-1-methoxymethyl-3,5-pyridinedicarboxylate obtained in Example 6, and 100 mg of Lipase B was added thereto, followed by stirring at 25° C. for 4 hours. Any insoluble matter was removed by filtration and washed with dichloromethane. The filtrate was concentrated under reduced pressure. The residue was purified by silica gel column chromatography (ethyl acetate/hexane=1/1) to obtain 405 mg (yield: 81%) of (+)-4-(2,3-dichlorophenyl)-1,4-dihydro-2,6-dimethyl-1-methoxymethyl-5-pivaloyloxymethoxycarbonyl-3-pyridinecarboxylic acid as a colorless crystal.

Melting point: 89°-90° C. (ethyl acetate/n-hexane)
[α]$_D$: +22.0° (c=1.0, acetone)
IR (nujol): 1750, 1705, 1685 cm$^{-1}$ $^1$H-NMR (CDCl$_3$) δ: 1.13 (9H, s, 3×CH$_3$) , 2.44 (6H, s, CH$_3$), 2.49 (3H, s, CH$_3$), 3.35 (3H, s, OCH$_3$), 4.78 (2H, s, NCH$_2$O), 5.52 (1H, s, >CH—), 5.75 (1H, d, J=5.4Hz, OCH$_A$H$_B$O), 6.99-7.27 (3H, m, C$_6$H$_3$)

$^{13}$C-NMR (CDCl$_3$) δ: 16.19, 16.26, 26.80 (3×C), 38.48, 38.67, 54.92, 77.32, 79.53, 106.50, 116.11, 127.04, 128.06, 128.96, 131.36, 133.27, 144.99, 149.13, 149.80, 166.17, 172.71, 177.09

TEST EXAMPLE 2

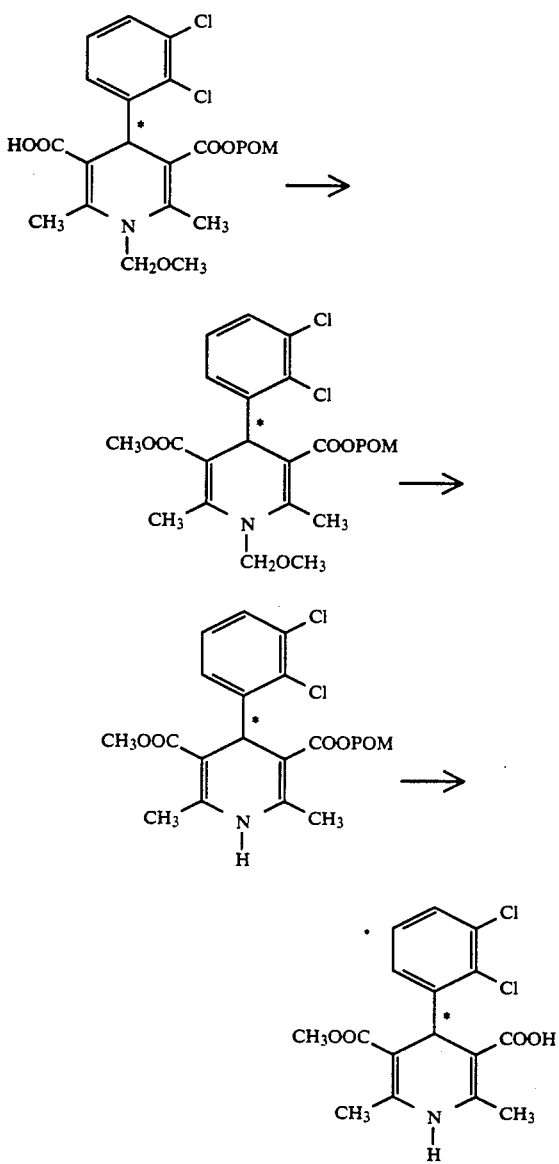

1) In 10 m; of dichloromethane was dissolved (+)-4-(2,3-dichlorophenyl)-1,4-dihydro-2,6-dimethyl -1-methoxymethyl-5-pivaloyloxymethylcarbonyl-3-pyridinecarboxylic acid obtained in Example 7, and 5 ml of a 0.5 M solution of diazomethane in diethyl ether was added thereto under ice-cooling, followed by stirring for 2 hours. Acetic acid was added to the reaction mixture until the yellow color disappeared, and the mixture was concentrated. The residue was purified by silica gel column chromatography (ethyl acetate/hexane=⅓) to obtain 236 mg (yield: 83%) of (+)-methyl pivaloyloxymethyl 4-(2,3-dichlorophenyl)-1,4-dihydro-2,6-dimethyl -1-methoxymethyl-3,5-pyridinedicarboxylate as a colorless crystal.

Melting point: 149°–150° C. (ethyl acetate/n-hexane)
$[\alpha]_D$: +26.0° (c=0.66, acetone)
IR (nujol): 1760, 1720, 1695 cm$^{-1}$
$^1$H-NMR (CDCl$_3$) δ: 1.12 (9H, s, 3×CH$_3$), 2.44 (3H, s, CH$_3$), 2.48 (3H, s, CH$_3$), 3.36 (3H, s, OCH$_3$), 3.66 (3H, s, COOCH$_3$), 4.80 (2H, s, NCH$_2$O), 5.53 (1H, s, >CH—), 5.74 (1H, d, J=5.4Hz, OCH$_A$H$_B$O), 5.78 (1H, d, J=5.4Hz, OCH$_A$H$_B$O), 7.00–7.06, 7.11–7.15, 7.23–7.27 (3H, m, C$_6$H$_3$)
$^{13}$C-NMR (CDCl$_3$) δ: 15.89, 16.20, 26.79 (3×C), 38.11, 38.64, 51.36, 54.95, 77.15, 79.39, 106.26, 108.18, 127.19, 128.55, 128.58, 130.99, 133.12, 145.80, 146.76, 149.73, 166.08, 168.08, 177.00

An aliquot of the product (non-recrystallized) was treated with a potassium hydroxide solution in methanol to obtain 4-(2,3-dichlorophenyl)-1,4-dihydro -2,6-dimethyl-5-methoxycarbonyl-1-methoxymethyl -3,5-pyridinecarboxylic acid, which was then reacted with phenyldiazomethane to obtain benzyl methyl 1,4-dihydro -2,6-dimethyl-1-methoxymethyl-4-(2,3- dichlorophenyl)-3,5-pyridinedicarboxylate. HPLC (isopropanol/hexane=1/10) using CHIRALCEL OD revealed that the product had an optical purity of 96% ee.

Melting point: 100°–101° C. (ethyl acetate/n-hexane)
IR (nujol): 1700, 1690 cm$^{-1}$
$^1$H-NMR (CDCl$_3$) δ: 2.42 (3H, s, CH$_3$), 2.47 (3H, s, CH$_3$), 3.35 (3H, s, OCH$_3$), 3.64 (3H, s, COOCH$_3$), 4.79 (2H, s, NCH$_2$O), 5.11 (2H, s, CH$_2$Ph), 5.54 (1H, s, >CH—), 6.98–7.03, 7.10–7.36 (8H, m, C$_6$H$_3$ and C$_6$H$_5$)
$^{13}$C-NMR (CDCl$_3$) δ: 15.96, 16.02, 38.36, 51.32, 54.94, 65.93, 77.07, 107.53, 107.85, 127.21, 127.84, 128.05 (2×C), 128.35 (2×C), 128.46, 128.49, 130.94, 133.03, 136.32, 146.16, 146.81, 147.95, 167.40, 168.26

2) In 7 ml of acetone was dissolved 190 mg of the (+)-methyl pivaloyloxymethyl 4-(2,3-dichlorophenyl) -1,4-dihydro-2,6-dimethyl-1-methoxymethyl -3,5-pyridinecarboxylic acid prepared in (1) above, and 0.3 ml of concentrated hydrochloric acid was added thereto. After stirring for 1 hour, the reaction mixture was neutralized with a 1N sodium hydroxide aqueous solution under cooling with ice, followed by concentration under reduced pressure. The residue was diluted with dichloromethane, washed successively with water and a saturated sodium chloride aqueous solution, and dried over anhydrous magnesium sulfate. Magnesium sulfate was removed by filtration, and the filtrate was concentrated under reduced pressure. The residue was subjected to preparative thin layer chromatography (TLC) (ethyl acetate/hexane=1/1), and the spot of the desired product was extracted with ethyl acetate. The extract was concentrated under reduced pressure to obtain 170 mg (yield: 98%) of (+)-methyl pivaloyloxymethyl 4-(2,3-dichlorophenyl)-1,4-dihydro-2,6-dimethyl-3,5-pyridinedicarboxylate as a colorless crystal.

Melting point: 154°–155° C. (acetone/n-hexane)
$[\alpha]_D$: +18.3° (c=1.0, acetone)
IR (nujol): 3340, 1740, 1710, 1690 cm$^{-1}$
$^1$H-NMR (CDCl$_3$) δ: 1.11 (9H, s, 3×CH$_3$), 2.30 (3H, s, CH$_3$), 2.32 (3H, s, CH$_3$), 3.60 (3H, s, COOCH$_3$), 5.47 (1H, s, >CH—), 5.71 (1H, d, J=5.5Hz, OCH$_A$H$_B$O, 5.74 (1H, d, J=5.5Hz, OCH$_A$H$_B$O), 5.94 (1H, s, NH), 7.03–7.09, 7.23–7.30 (3H, m, C$_6$H$_3$)
$^{13}$C-NMR (CDCl$_3$) δ: 19.30, 19.91, 26.79 (3×C), 30.06, 38.61, 50.94, 79.06, 102.12, 103.92, 126.98, 128.37, 129.83, 131.24, 132.98, 143.91, 146.38, 147.47, 165.76, 167.68, 177.11

3) To 2 ml of methanol having dissolved therein 20 mg of potassium hydroxide was added dropwise a solution of 142 mg of the (+)-methyl pivaloyloxymethyl 4-(2,3-dichlorophenyl) -1,4-dihydro-2,6-dimethyl-3,5-pyridinedicarboxylate obtained in (2) above in 2 ml of methanol, followed by stirring for 2 hours. The reaction mixture was neutralized with acetic acid and then concentrated under reduced pressure. The residue was subjected to preparative TLC and the spot of the desired product was extracted with ethyl acetate. The extract was concentrated under reduced pressure to obtain 96 mg (yield: 90%) of (+)-4-(2,3-dichlorophenyl) -1,4-dihydro-2,6-dimethyl-5-methoxycarbonyl -3-pyridinecarboxylic acid as a colorless crystal.

Melting point: 186°-187° C. (acetone/n-hexane)
[α]$_D$: +5.2° (c=0.7, acetone)
IR (nujol): 3350, 1700, 1685 cm$^{-1}$ $^1$H-NMR (acetone-d$_6$) δ: 2.30 (3H, s, CH$_3$), 2.32 (3H, s, CH$_3$), 3.55 (3H, s, OCH$_3$), 5.51 (1H, s, >CH—), 7.16-7.21, 7.30-7.34, 7.42-7.46 (3H, m, C$_6$H$_3$), 7.98 (1H, s, NH), 10.0-10.5 (1H, br, COOH)

$^{13}$C-NMR (acetone-d$_6$) δ: 18.58, 18.81, 39.93, 50.73, 103.17, 103.20, 128.26, 128.90, 130.94, 131.47, 133.03, 146.27, 146.50, 150.02, 168.20, 169.13

EXAMPLE 8

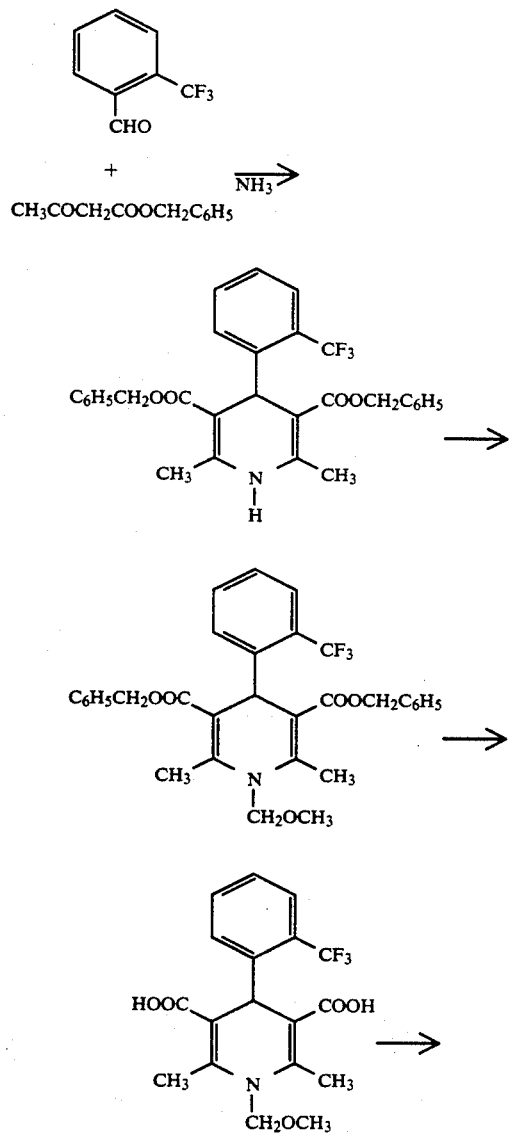

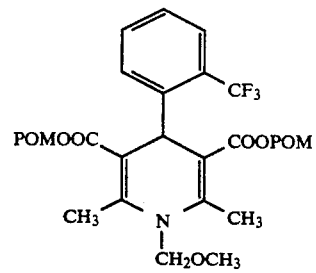

1) In a 7% ammonia solution in methanol were dissolved 2.6 g of o-trifluoromethylbenzaldehyde and 5.8 g of benzyl acetoacetate, and the solution was stirred in a closed tube at 90° C. for 10 hours. The reaction mxiture was concentrated under reduced pressure, and the residue was purified by silica gel column chromatography (methanol/dichloromethane =1/50) to obtain 6.0 g (yield: 76%) of dibenzyl 1,4-dihydro -2,6-dimethyl-4-(2-trifluoromethylphenyl)-3,5-pyridinedicarboxylate as a yellow oily substance.

IR (neat): 3340, 1680 cm$^{-1}$ $^1$H-NMR (CDCl$_3$) δ: 2.13 (6H, s, 2×CH$_3$), 4.97 (2H, d, J=12.7Hz, OCH$_A$H$_B$O), 5.15 (2H, d, J=12.7Hz, OCH$_A$H$_B$O), 5.65 (1H, s, NH), 6.21 (1H, s, NH), 7.11-7.52 (14H, m, C$_6$H$_4$ and 2×C$_6$H$_5$)

$^{13}$C-NMR (CDCl$_3$) δ: 19.24 (2×C), 36.06, 65.37 (2×C), 104.50 (2×C), 125.21 (q, J=275Hz), 126.46, 126.53, 126.88 (q, J=30.0Hz), 127.69 (2×C), 127.77 (4×C), 128.29 (4×C), 131.27, 131.94, 136.71 (2×C), 144.29, 147.15 (2×C), 167.39 (2×C)

2) In 50 ml of dried tetrahydrofuran solution was dissolved 4.7 g of the dibenzyl 1,4-dihydro-2,6-dimethyl-4-(2-trifluoromethylphenyl)-3,5-pyridinedicarboxylate obtained in (1) above, and 1.1 g of 60% oily sodium hydride was slowly added thereto with stirring while cooling with ice. After stirring for 10 minutes, 1.1 g of chloromethyl ether was added thereto dropwise under ice-cooling, followed by stirring at 0° C. for 3 hours. After completion of the reaction, 2 ml of acetic acid was added to the reaction mixture, and the mixture was concentrated under reduced pressure. The resulting residue was diluted with ethyl acetate, washed successively with water, a saturated sodium hydrogencarbonate aqueous solution, and a saturated sodium chloride aqueous solution, and dried over anhydrous sodium sulfate. After removing the drying agent by filtration, the filtrate was concentrated under reduced pressure. The residue was subjected to silica gel column chromatography (ethyl acetate/hexane=3/7) to obtain 2.8 g (yield: 56%) of dibenzyl 1,4-dihydro-2,6-dimethyl-1-methoxymethyl-4-(2-trifluoromethylphenyl) -3,5-pyridinedicarboxylate as a colorless crystal.

Melting point: 94°-95° C. (acetone/n-hexane)
IR (nujol): 1700 cm$^{-1}$ $^1$H-NMR (CDCl$_3$) δ: 2.37 (6H, s, 2×CH:), 3.33 (3H, s, OCH$_3$), 4.78 (2H, s, NCH$_2$O), 5.00 (2H, d, J=12.2Hz, OCH$_A$H$_B$O), 5.16 (2H, d, J=12.2Hz, OCH$_A$H$_B$O), 5.56 (1H, s, NH), 7.16-7.52 (14H, m, C$_6$H$_5$ and 2×C$_6$H$_4$)

$^{13}$C-NMR (CDCl$_3$) δ: 15.92 (2×C), 36.37, 54.98, 65.89 (2×C), 76.97, 108.93 (2×C), 124.55 (q, J=274Hz), 126.08 (q, J=5.7Hz), 126.59, 126.93 (q, J=30.1Hz), 127.74 (2×C), 127.92 (4×C), 128.29 (4×C), 130.44, 132.25, 136.34 (2×C), 144.78, 147.57 (2×C), 167.82 (2×C)

3) In 100 ml of ethanol was dissolved 2.8 g of the dibenzyl 1,4-dihydro-2,6-dimethyl-4-(2-trifluoromethylphenyl)-3,5-pyridinedicarboxylate obtained in (2) above, and the solution was subjected to catalytic reduction in a hydrogen stream using 420 mg of palladium-on-carbon as a catalyst. The catalyst was removed by filtration, and the filtrate was concentrated under reduced pressure. The resulting crude crystal was recrystallized from methanol/hexane to obtain 1.2 g (yield: 62%) of 1,4-dihydro-2,6-dimethyl-1-methoxymethyl-4-(2-trifluoromethylphenyl) -3,5-pyridinedicarboxylic acid as a colorless crystal.

Melting point: 172°-173° C. (methanol/n-hexane)
IR (nujol): 1670 cm$^{-1}$
$^1$H-NMR (CDCl$_3$) δ: 2.40 (6H, s, 2×CH$_3$), 3.34 (3H, s, OCH$_3$), 4.90 (2H, s, NCH$_2$O), 5.46 (1H, s, >CH—), 7.24–7.52 (4H, m, C$_6$H$_4$)
$^{13}$C-NMR (CDCl$_3$) δ: 16.14 (2×C), 38.14, 58.36, 78.01, 110.42 (2×C), 126.07 (q, J=274Hz), 126.92 (q, J=5.7Hz), 127.74, 128.47, 131.92, 133.35, 146.71 (3×C), 172.10 (2×C)

4) In 5 ml of dimethylformamide was dissolved 770 mg of 1,4-dihydro-2,6-dimethyl-1-methoxymethyl-4-(2-trifluoromethylphenyl)-3,5-pyridinedicarboxylic acid obtained in (3) above, and 200 mg of 60% oily sodium hydride was added thereto at 0° C. in an argon stream with stirring. After stirring for 20 minutes, 750 mg of chloromethyl pivalate was added thereto dropwise, followed by stirring at room temperature for 3 hours. The reaction mixture was neutralized with 6N hydrochloric acid, diluted with dichloromethane, washed successively with water and a saturated sodium chloride aqueous solution, and dried over anhydrous magnesium sulfate. Magnesium sulfate was removed by filtration, and the filtrate was concentrated under reduced pressure. The residue was subjected to silica gel column chromatography (ethyl acetate/hexane=¼) to obtain 760 mg (yield: 62%) of bis(pivaloyloxymethyl) 1,4-dihydro-2,6-dimethyl-1-methoxymethyl-4-(2-trifluoromethylphenyl)-3,5-pyridinedicarboxylate as a pale yellow crystal.

Melting point: 96°-97° C. (acetone/n-hexane)
IR (nujol): 1750, 1720 cm$^{-1}$
$^1$H-NMR (CDCl$_3$) δ: 1.13 (18H, s, 6×CH$_3$), 2.41 (6H, s, 2×CH$_3$), 3.38 (3H, s, OCH$_3$), 4.82 (2H, s, NCH$_2$O), 5.48 (1H, s, >CH—), 5.70 (2H, d, J=5.4Hz, OCH$_A$H$_B$O), 5.76 (2H, d, J=5.4Hz, OCH$_A$H$_B$O), 7.27–7.54 (4H, m, C$_6$H$_4$)
$^{13}$C-NMR (CDCl$_3$) δ: 16.06 (2×C), 26.79 (2×C), 35.88, 38.66 (2×C), 55.04, 77.10, 79.75 (2×C), 108.21 (2×C), 124.50 (q, J=274Hz), 126.28 (q, J=5.3Hz), 126.82, 126.92 (q, J=30.1Hz), 130.38, 132.20, 144.15, 147.13 (2×C), 166.37 (2×C), 176.94 (2×C)

EXAMPLE 9

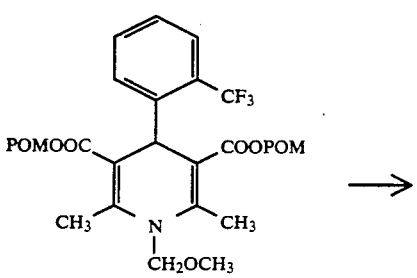

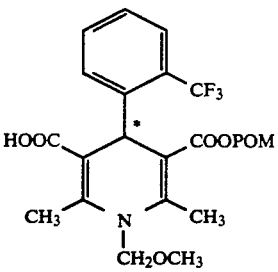

In 10 ml of isopropyl ether saturated with water was dissolved 613 mg of bis(pivaloyloxymethyl) 1,4-dihydro-2,6-dimethyl-1-methoxymethyl-4-(2-trifluoromethylphenyl)-3,5-pyridinedicarboxylate obtained in Example 8, and 50 mg of Lipase B was added thereto, followed by stirring at room temperature for 7 hours. Any insoluble matter was removed by filtration and washed with dichloromethane. The filtrate was concentrated under reduced pressure. The residue was subjected to preparative TLC (acetate/hexane=1/1), and the spot of the desired product was extracted with ethyl acetate. The extract with concentrated under reduced pressure to obtain 414 mg (yield: 84%) of (+)-1,4-dihydro-2,6-dimethyl -1-methoxymethyl-4-(trifluoromethylphenyl)-5-pivaloyloxymethoxycarbonyl -3-pyridinecarboxylic acid as a colorless crystal.

Melting point: 69°-70° C. (methanol)
[α]$_D$: +33.8° (c=1.6, acetone)
IR (nujol): 1765, 1745, 1700 cm$^{-1}$
$^1$H-NMR (CDCl$_3$) δ: 1.13 (9H, s, 3×CH$_3$), 2.39 (6H, s, CH$_3$), 2.47 (3H, s, CH$_3$), 3.37 (3H, s, OCH$_3$), 4.81 (2H, s, NCH$_2$O), 5.52 (1H, s, >CH—), 5.70 (1H, d, J=5.5Hz, OCH$_A$H$_B$O), 5.77 (1H, d, J=5.5Hz, OCH$_A$H$_B$O), 7.22–7.52 (4H, m, C$_6$H$_4$)
$^{13}$C-NMR (CDCl$_3$) δ: 16.09, 16.14, 26.80 (3×C), 35.94, 38.67, 55.04, 77.15, 79.84, 108.18, 108.50, 124.55 (q, J=274Hz), 126.49 (q, J=5.2Hz), 126.75, 127.27 (q, J=30.1Hz), 130.29, 132.02, 144.21, 146.93, 148.23, 166.51, 172.49, 177.02

TEST EXAMPLE 3

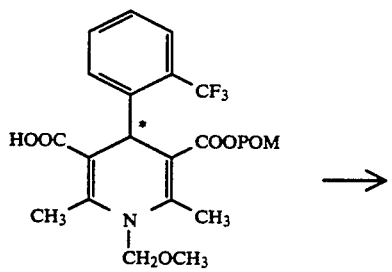

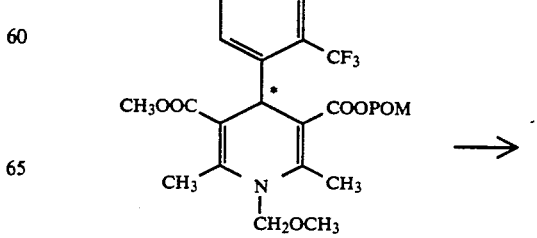

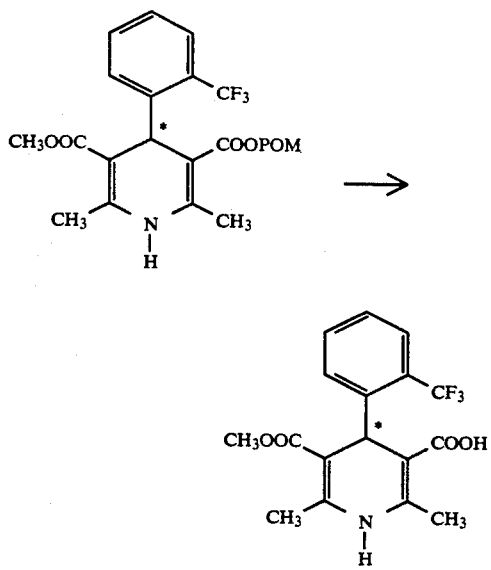

1) In 3 ml of dichloromethane was dissolved 70 mg of (+)-1,4-dihydro-2,6-dimethyl-1-methoxymethyl-4-(2-trifluoromethylphenyl) -5-pivaloyloxymethylcarbonyl-3-pyridinecarboxylic acid obtained in Example 9, and 2 ml of a 0.5 M solution of diazomethane in diethyl ether was added thereto under ice-cooling, followed by stirring for 1 hour. Acetic acid was added to the reaction mixture until the yellow color disappeared, and the mixture was concentrated. The residue was subjected to preparative TLC (ethyl acetate /hexane=⅓), and the spot of the desired product was extracted with ethyl acetate. The extract was concentrated under reduced pressure to obtain 70 mg (yield: 97%) of (+)-methyl pivaloyloxymethyl 1,4-dihydro-2,6-dimethyl-1-methoxymethyl-4-(2-trifluoromethylphenyl) -3,5-pyridinedicarboxylate as a colorless crystal.

Melting point: 110°–112° C. (acetone/n-hexane)

[α]$_D$: +17.1° (c=1.1, acetone)

IR (nujol): 1760, 1720, 1700 cm$^{-1}$ $^1$H-NMR (CDCl$_3$) δ: 1.12 (9H, s, 3×CH$_3$), 2.39 (3H, s, CH$_3$), 2.44 (3H, s, CH$_3$), 3.38 (3H, s, OCH$_3$), 3.63 (3H, s, COOCH$_3$), 4.83 (2H, s, NCH$_2$O), 5.47 (1H, s, >CH—), 5.70 (1H, d, J=5.3Hz, OCH$_A$H$_B$O), 5.76 (1H, d, J=5.3Hz, OCH$_A$H$_B$O), 7.27–7.53 (3H, m, C$_6$H$_4$)

$^{13}$C-NMR (CDCl$_3$) δ: 15.86, 16.10, 26.78 (3×C), 35.93, 38.65, 51.29, 55.03, 77.05, 79.63, 107.72, 109.64, 124.59 (q, J=274Hz), 126.24 (q, J=5.7Hz), 126.74, 126.86 (q, J=30.5Hz), 130.40, 132.21, 144.67, 145.02, 148.06, 166.39, 168.42, 176.96

An aliquot of the resulting compound (non-recrystallized) was treated with a methanol solution of potassium hydroxide to obtain 1,4-dihydro-2,6-dimethyl -5-methoxycarbonyl-1-methoxymethyl-4-(2-trifluoromethylphenyl)-5-methoxycarbonyl -3-pyridinecarboxylic acid, which was then reacted with phenyldiazomethane to obtain benzyl methyl 1,4-dihydro-2,6-dimethyl-1-methoxymethyl-4-(2-trifluoromethylphenyl)-3,5-pyridinedicarboxylate. HPLC (isopropyl alcohol/hexane=1/10) using CHIRALCEL OD of the product revealed that the optical purity was 99% ee.

IR (neat): 1720, 1700 cm$^{-1}$ $^1$H-NMR (CDCl$_3$) δ: 2.40 (6H, s, 2×CH$_3$), 3.37 (3H, s, OCH$_3$), 3.62 (3H, s, COOCH$_3$), 4.81 (2H, s, NCh$_2$O), 5.02 (1H, d, J=12.5Hz, CH$_2$Ph), 5.16 (1H, d, J=12.5Hz, CHzPh), 5.50 (1H, s, >CH—), 7.17–7.52 (9H, m, C$_6$H$_4$ and C$_6$H$_5$)

$^{13}$C-NMR (CDCl$_3$) δ: 15.92, 16.01, 36.35, 51.30, 54.88, 65.33, 76.86, 108.82, 108.95, 124.33 (q, J=274Hz), 126.10 (q, J=5.8Hz), 126.60, 126.88 (q, J=30.0Hz), 127.70, 127.90 (2×C), 128.26 (2×C), 130.45, 132.26, 136.38, 144.81, 144.83, 145.58, 167.80, 168.40

2) To 5 ml of acetone containing 2 ml of 2N hydrochloric acid was added 256 mg of the (+)-methylpivaloyloxymethyl 1,4-dihydro-2,6-dimethyl -1-methoxymethyl-4-(2-trifluoromethylphenyl) -3,5-pyridinedicarboxylate obtained in (1) above, and the mixture was stirred for 2 hours. The reaction mixture was neutralized with a 1N sodium hydroxide aqueous solution under cooling with ice, followed by concentration under reduced pressure. The residue was extracted twice with dichloromethane, and the extract was dried over anhydrous magnesium sulfate and concentrated. The residue was subjected to preparative TLC (ethyl acetate/hexane =1/1), and the spot of the desired product was extracted with ethyl acetate. The extract was concentrated under reduced pressure to obtain 220 mg (yield: 94%) of (+)-methyl pivaloyloxymethyl 1,4-dihydro-2,6-dimethyl -4-(2-trifluoromethylphenyl)-3,5-pyridinedicarboxylate as a pale yellow oily substance.

[α]$_D$: +25.2° (c=0.8, acetone)

IR (neat): 3340, 1750, 1720, 1705 cm$^{-1}$ $^1$H-NMR (CDCl$_3$) δ: 1.11 (9H, s, 3×CH$_3$), 2.29 (3H, s, CH$_3$), 2.31 (3H, s, CH$_3$), 3.58 (3H, s, COOCH$_3$), 5.57 (1H, s, >CH—), 5.66 (1H, d, J=5.5Hz, OCH$_A$H$_B$O), 5.74 (1H, d, J=5.5Hz, OCH$_A$H$_B$O), 6.00 (1H, s NH), 7.21–7.24, 7.38–7.41, 7.47–7.51 (4H, m, (6H$_4$)

$^{13}$C-NMR (CDCl$_3$) δ: 19.19, 19.85, 26.78 (3×C), 35.53, 38.67, 50.86, 79.40, 103.60, 105.43, 125.18 (q, J=275Hz), 126.54, 126.60 (q, J=4.8Hz), 126.93 (q, J=30.0Hz), 131.22, 131.89, 143.33, 145.95, 146.73, 165.83, 167.87, 177.15

3) To 10 ml of methanol having dissolved therein 560 mg of potassium hydroxide was added 94 mg of the (+)-methylpivaloyloxymethyl 1,4-dihydro-2,6-dimethyl-4-(2-trifluoromethylphenyl)-3,5-pyridinedicarboxylate obtained in (2) above, followed by stirring for 3 hours. The reaction mixture was neutralized with acetic acid under ice-cooling and concentrated under reduced pressure. The residue was extracted with ethyl acetate, and the extract was dried over anhydrous magnesium sulfate and concentrated. The residue was subjected to preparative TLC (methanol/dichloromethane=1/30), and the spot of the desired product was extracted with dichloromethane. The extract was concentrated under reduced pressure to obtain 43 mg (yield: 60%) of (+)-1,4-dihydro-2,6-dimethyl-4-(2-trifluoromethylphenyl) -5-methoxycarbonyl-3-pyridinecarboxylic acid as a colorless crystal.

Melting point: 109° ∝ 110° C. (acetone/n-hexane)

[α]$_D$:+24.4° (c=0.6, acetone)

IR (nujol): 3320, 1710, 1690 cm$^{-1}$ $^1$H-NMR (acetone-d$_6$) δ: 2.30 (3H, s, CH$_3$), 2.32 (3H, s, CH$_3$), 3.51 (3H, s, OCH$_3$), 5.59 (1H, s, >CH—), 7.27–7.67 (4H, m, C$_6$H$_5$), 7.88 (1H, s, NH), 10.0–10.3 (1H, br, COOH)

$^{13}$C-NMR (acetone-d$_6$) δ: 18.64, 18.81, 36.90, 50.62, 104.62, 104.86, 126.34 (q, J=275Hz), 127.03 (q, J=4.8Hz), 127.21, 127.59 (q, J=30.0Hz), 132.29, 132.85, 145.81, 145.83, 149.16, 168.27, 169.08

EXAMPLE 10

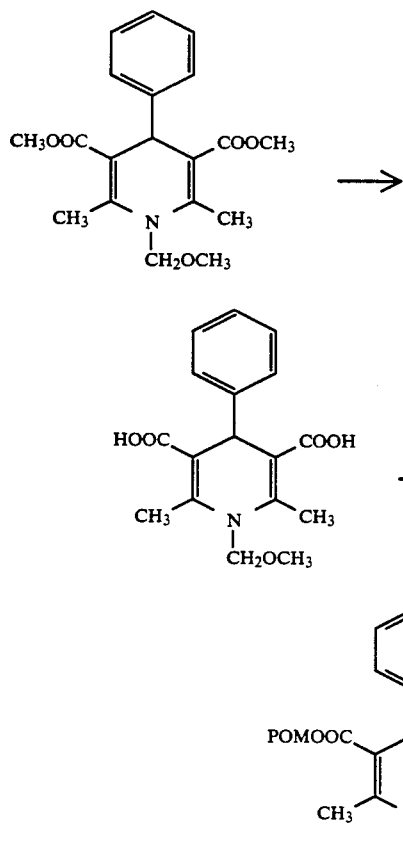

1) In 40 ml of methanol were dissolved 3.0 g of potassium hydroxide and 770 mg of benzyltributylammonium bromide, and 3.9 g of dimethyl 1,4-dihydro-2,6-dimethoxy-1-methoxymethyl-4-phenyl-3,5-pyridinedicarboxylate was added to the solution, followed by refluxing for 72 hours. Ten milliliters of water were added to the reaction mixture, and the mixture was made acidic (pH=1 to 2) with concentrated hydrochloric acid. The thus formed pale yellow precipitate was collected by filtration, washed with cold ethanol, and dried to obtain 3.0 g (yield: 86%) of 1,4-dihydro-2,6-dimethyl -1-methoxymethyl-4-phenyl-3,5-pyridinedicarboxylic acid as a pale yellow powder.

Melting point: 174°-176° C. (methanol)
IR (nujol): 1670 cm$^{-1}$
$^1$H-NMR (CD$_3$OD) δ: 2.50 (6H, s, 2×CH$_3$), 3.21 (3H, s, OCH$_3$), 4.82 (2H, s, NCH$_3$O), 5.13 (1H, s, >CH—), 7.06-7.30 (5H, m, C$_6$H$_5$)
$^{13}$C-NMR (CD$_3$OD) δ: 18.73 (2×C), 40.86, 54.95, 78.20, 104.06 (2×C) 126.88, 128.18, 128.70, 128.83, 129.02, 147.08, 149.73 (2×C), 171.88 (2×C)

2) In 3 ml of dimethylformamide was dissolved 1.4 g of the resulting 1,4-dihydro-2,6-dimethyl-1-methoxymethyl-4-phenyl-3,5-pyridinedicarboxylic acid obtained in (1) above, and 1.7 g of diisopropylethylamine and 1.6 g of chloromethyl pivalate were added thereto dropwise at 0° C. in an argon stream, followed by stirring at room temperature for 15 hours. The reaction mixture was diluted with dichloromethane, washed successively with water and a saturated sodium chloride aqueous solution, and dried over anhydrous magnesium sulfate. Magnesium sulfate was removed by filtration, and the filtrate was concentrated under reduced pressure. The residue was purified by silica gel column chromatography (ethyl acetate/hexane=2/5) to obtain 1.7 g (yield: 71%) of bis(pivaloyloxymethyl) 1,4-dihydro-2,6-dimethyl-1-methoxymethyl -4-phenyl-3,5-pyridinedicarboxylate as a colorless crystal.

Melting point: 89°-90° C. (isopropyl ether/n-hexane)
IR (nujol): 1750, 1740, 1705 cm$^{-1}$
$^1$H-NMR (CDCl$_3$) δ: 1.14 (18H, s, 6×CH$_3$), 2.51 (6H, s, 2×CH$_3$), 3.26 (3H, s, OCH$_3$), 4.75 (2H, s, NCH$_2$O), 5.09 (1H, s, >CH—), 5.77 (2H, d, J=5.5Hz, OCH$_A$H$_B$O), 5.85 (2H, d, J=5.5Hz, OCH$_A$H$_B$O), 7.10-7.16 (4H, m, C$_6$H$_5$)
$^{13}$C-NMR (CDCl$_3$) δ: 16.21 (2×C), 26.82 (2×C), 38.14, 38.70 (2×C), 54.86, 77.30, 79.40, 107.39 (2×C), 126.39, 127.10, 127.19, 128.18, 128.21, 145.01, 150.04 (2×C), 165.99 (2×C), 177.06 (2×C)

EXAMPLE 11

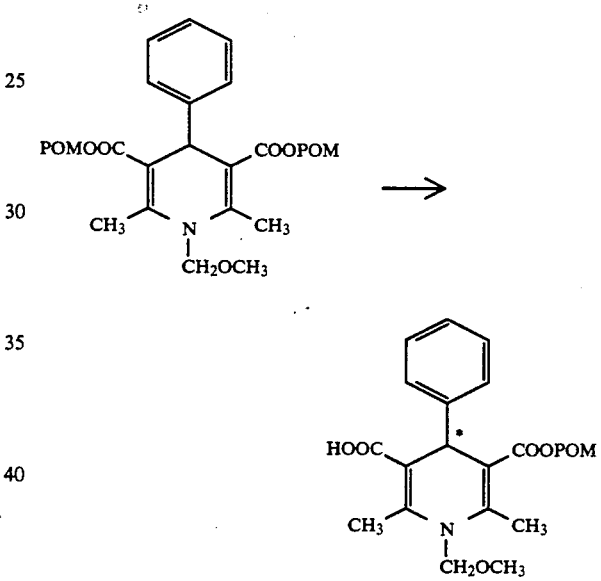

To 20 ml of isopropyl ether saturated with water were added 545 mg of bis(pivaloyloxymethyl) 1,4-dihydro -2,6-dimethyl-1-methoxymethyl-4-phenyl-3,5-pyridinedicarboxylate obtained in Example 10 and 100 mg of Lipase B, and the system was stirred at 25° C. for 5 hours. Any insoluble matter was removed by filtration and washed with dichloromethane. The filtrate was concentrated under reduced pressure. The residue was subjected to silica gel column chromatography (ethyl acetate/hexane=1/1) to obtain 328 mg (yield: 76%) of (+)-1,4-dihydro-2,6-dimethyl-1-methoxymethyl -4-phenyl-5-pivaloyloxymethoxycarbonyl -3-pyridinecarboxylic acid as a colorless crystal.

Melting point: 121°-122° C. (acetone/n-hexane)
[α]$_D$: +43.5° (c=1.5, acetone)
IR (nujol): 1750, 1720, 1680 cm$^{-1}$
$^1$H-NMR (CDCl$_3$) δ: 1.14 (9H, s, 3×CH$_3$), 2.51 (3H, s, CH$_3$), 2.53 (3H, s, CH$_3$), 3.24 (3H, s, OCH$_3$), 4.73 (2H, s, NCH$_2$O), 5.14 (1H,s, >CH—), 5.77 (1H, d, J=5.5Hz, OCH$_A$H$_B$O), 5.85 (1H, d, J=5.5Hz, OCH$_A$H$_B$O), 7.10-7.20 (5H, m, C$_6$H$_5$)
$^{13}$C-NMR (CDCl$_3$) δ: 16.19, 16.25, 37.92, 38.71, 77.29, 79.36, 107.44, 107.49, 126.36, 127.04, 127.14, 128.21 (2×C), 144.93, 150.29, 150.70, 166.00, 173.15, 177.14

TEST EXAMPLE 4

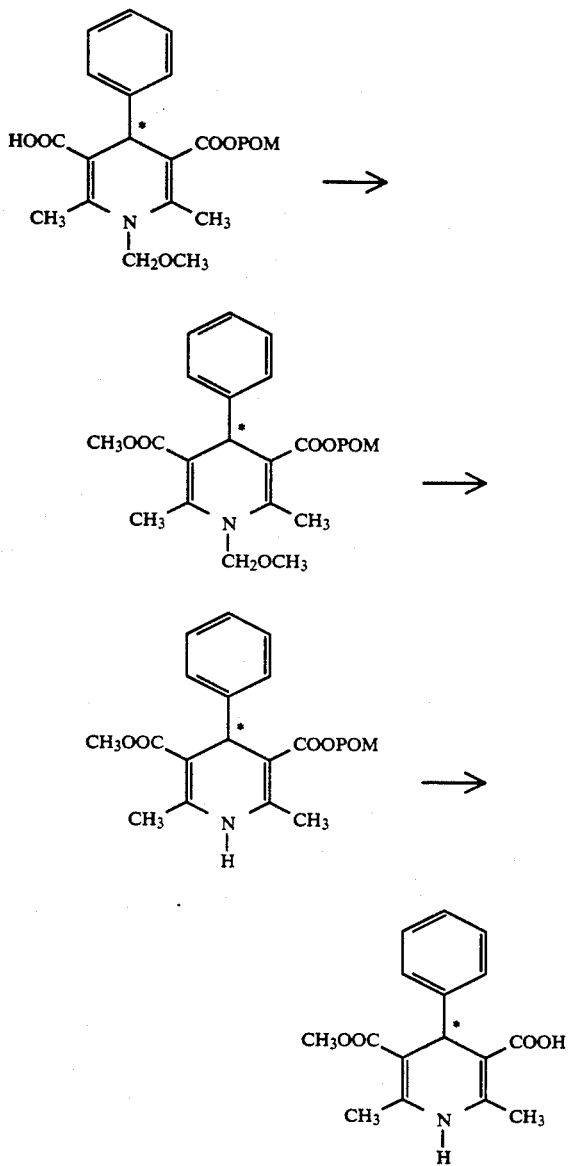

1) In 5 ml of dichloromethane was dissolved 216 mg of (+)-1,4-dihydro-2,6-dimethyl-1--methoxymethyl-4-phenyl-5-pivaloyloxymethylcarbonyl -3-pyridinecarboxylic acid obtained in Example 11, and 6 ml of a diazomethane solution in diethyl either was added thereto under ice-cooling, followed by stirring for 1 hour. Acetic acid was added to the reaction mixture until the yellow color disappeared, and the mixture was concentrated. The resulting residue was subjected to preparative TLC (ethyl acetate/hexane=½), and the spot of the desired product was extracted with ethyl acetate. The extract was concentrated under reduced pressure to obtain 220 mg (yield: 99%) of (+)-methyl pivaloyloxymethyl 1,4-dihydro-2,6-dimethyl-1-methoxymethyl -4-phenyl-3,5-pyridinedicarboxylate as a colorless crystal.

Melting point: 80°-81° C. (acetone/n-hexane)

$[\alpha]_D$: +30.2° (c=1.0, acetone)

IR (nujol): 1750, 1705, 1685 cm$^{-1}$ $^1$H-NMR (CDCl$_3$) δ: 1.15 (9H, s, 3×CH$_3$), 2.50 (3H, s, CH$_3$) , 2.51 (3H, s, CH$_3$), 3.23 (3H, s, OCH$_3$), 3.68 (3H, s, COOCH$_3$), 4.74 (2H, s, NCH$_2$O), 5.11 (1H, s, >CH—), 5.79 (1H, d, J=5.6Hz, OCH$_A$H$_B$O), 5.86 (1H, d, J=5.6Hz, OCH$_A$H$_B$O), 7.13-7.18 (5H, m, C$_6$H$_5$)

$^{13}$C-NMR (CDCl$_3$) δ: 15.91, 16.23, 26.80 (3×C), 38.22, 38.69, 51.34, 54.78, 77.24, 79.18, 106.78, 108.44, 126.23, 126.30, 126.99, 127.08, 128.17, 145.25, 148.18, 150.55, 166.09, 168.03, 177.12

An aliquot of the resulting product (non-recrystallized) was treated with a methanol solution of potassium hydroxide to obtain 1,4-dihydro-2,6-dimethyl -5-methoxycarbonyl-1-methoxymethyl-4-phenyl-3-pyridinecarboxylic acid, which was then reacted with phenyldiazomethane to obtain benzyl methyl 1,4-dihydro-2,6-dimethyl-1-methoxymethyl-4-phenyl-3,5-pyridinedicarboxylate. HPLC (isopropanol/hexane=1/10) using CHIRALCEL OD of the product revealed that the optical purity was 99% ee.

Melting point: 84°-85° C. (acetone/n-hexane)

IR (nujol): 1705, 1700 cm$^{-1}$ $^1$H-NMR (CDCl$_3$) δ: 2.46 (3H, s, CH$_3$), 2.51 (3H, s, Ch$_3$), 3.22 (3H, s, OCH$_3$), 3.68 (3H, s, COOCH$_3$), 4.73 (2H, s, NCH$_2$O), 5.11 (1H, d, J=12.4Hz, CH$_2$Ph), 516 (1H, s, >CH—), 5.21 (1H, d, J=12.4Hz, CH$_2$Ph), 7.10-7.36 (10H, m, C$_6$H$_5$)

$^{13}$C-NMR (CDCl$_3$) δ: 16.02, 16.13, 38.56, 51.32, 54.77, 65.84, 77.22, 107.90, 108.13, 126.22 (2×C), 127.19 (2×C), 127.83 (2×C), 128.13 (2×C), 128.38 (2×C), 136.52, 145.51, 148.90, 167.52, 168.24

2) In 5 ml of acetone containing 1 ml of 2N hydrochloric acid was added 200 mg of (+) -methyl pivaloyloxymethyl 1,4-dihydro -2,6-dimethyl-1-methoxymethyl-4-phenyl-3,5-pyridinedicarboxylate obtained in (1) above, and the mixture was stirred for 2 hours. The reaction mixture was neutralized with a 1N sodium hydroxide aqueous solution under ice-cooling and concentrated under reduced pressure. The residue was extracted twice with dichloromethane, and the extract was dried over anhydrous magnesium sulfate. Magnesium sulfate was removed by filtration, and the filtrate was concentrared under reduced pressure. The residue was subjected to silica gel column chromatography (ethyl acetate/hexane=½) to obtain 177 mg (yield: 98%) of (+)-methyl pivaloyloxymethyl 1,4-dihydro-2,6-dimethyl-4-phenyl -3,5-pyridinedicarboxylate as a colorless crystal.

Meltting point: 81°-82° C. (acetone/n-hexane)

$[\alpha]_D$: +27.1° (c=0.8, acetone)

IR (nujol): 3390, 1750, 1710, 1700 cm$^{-1}$ $^1$H-NMR (CDCl$_3$) δ: 1.19 (9H, s, 3×CH$_3$), 2.31 (6H, s 2/1 ×CH$_3$), 3.62 (3H, s, COOCH$_3$), 4.98 (1H, s, >CH—), 5.74 (1H, d, J=5.4Hz, OCH$_A$H$_B$O), 5.78 (1H, d, J=5.4Hz, OCH$_A$H$_B$O), 6.14 (1H, s, NH), 7.11-7.26 (5H, m, C$_6$H$_5$)

$^{13}$C-NMR (CDCl$_3$) δ: 19.29, 19.78, 26.78, (3×C), 38.67, 39.10, 51.03, 78.87, 102.58, 104.37, 126.25, 127.70 (2×C), 128.03 (2×C), 143.99, 146.38, 147.19, 166.01, 167.97, 177.30

3) In a solution of 0.2 g of potassium hydroxide in 2 ml of methanol was dissolved 110 mg of (+) -methyl pivaloyloxymethyl 1,4-dihydro-2,6-dimethyl -4-phenyl-3,5-pyridinedicarboxylate obtained in (2) abvoe, followed by stirring for 3 hours. The reaction mixture was neutralized with 1 N hydrochloric acid under ice-cooling and concentrated under reduced pressure. The residue was diluted with ethyl acetate, washed successivley with water and a saturated sodium chloride aqueous solution, and dried over anhydrous magnesium sulfate. Magnesium sulfate was removed by filtration, and the filtrate was concentrated under reduced pressure. The residue was subjected to preparative TLC (ethyl acetate/hexane=1/1), and the spot of the desired product was extracted with ethyl acetate. The extract was concentrated under reduced pressure to obtain 69 mg (yield: 88%) of (−)-1,4-dihydro-2,6-dimethyl-4-phenyl-5-methoxycarbonyl-3-pyridinecarboxylic acid as a colorless crystal.

Melting point: 158°-159° C. (acetone/n-hexane)
$[\alpha]_D$: −10.3° (c=0.7, acetone)
Ir (nujol): 3330, 1675, 1650 cm$^{-1}$
$^1$H-NMR (acetone-d$_6$) δ: 2.33 (3H, s, CH$_3$), 2.34 (3H, s, Ch$_3$), 3.92 (3H, s, COOCH$_3$), 5.07 (1H, s, >CH—), 7.05-7.30 (5H, m, C$_6$H$_5$), 7.88 (1H, s, NH), 10.2-10.5(1H, br, COOH)
—C-NMR (acetone-d$_6$) δ: 18.93, 18.84, 40.28, 50.85, 103.56, 103.59, 125.70, 128.47, (2×C), 128.68 (2×C), 146.10, 146.47, 149.10, 168.44, 169.40

EXAMPLE 12

In 10 ml of dimethylformamide was dissolved 1.4 g of crude 1,4-dihydro-2,6-dimethyl-1-methoxymethyl-4(3-nitrophenyl)-3,5-pyridinedicarboxylic acid as obtained in Example 1-(1), and 1.4 g of diisopropylethylamine and 1.2 g of chloromethyl propionate were added to the solution under an argon stream, followed by stirring for 8 hours. The reaction mixture was filtered and washed with dichloromethane, and the filtrate was washed successively with water and a saturated sodium chloride aqueous soltuion, and dried over anhydrous magnesium sulfate. Magnesium sulfate was removed by filtration, and the filtrate was concentrated under reduced pressure. The residue was subjected to silica gel column chromatography (ethyl acetate/hexane=3/5) to obtain 790 mg (yield: 37%) of bis(propionyloxymethyl) 1,4-dihydro-2,6-dimethyl -1-methoxymethyl-4-(3-nitrophenyl)-3,5-pyridinedicarboxylate as a pale yellow crystal.

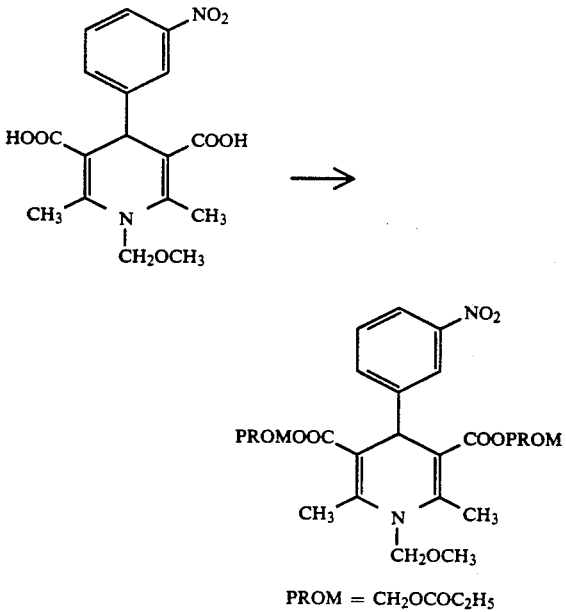

PROM = CH$_2$OCOC$_2$H$_5$

Melting point: 86°-87° C. (acetone/n-hexane)
IR (nujol): 1755, 1720 cm$^{-1}$
$^1$H-NMR (CDCl$_3$) δ: 1.10 (6H, t, J=7.3Hz, 2×CH$_2$CH$_3$), 2.31, 2.32 (4H, each q, J=7.3Hz, 2×OCH$_2$CH$_3$), 2.55 (6H, s, 2×CH$_3$), 3.35 (3H, s, OCH$_3$), 4.82 (2H, s, NCH$_2$O), 5.14 (1H, s, >CH—), 5.78 (2H, d, J=5.6Hz, OCH$_A$H$_B$O), 5.82 (2H, d, J=5.6Hz, OCH$_A$H$_B$O), 7.33-7.39, 7.57-7.59, 7.99-8.01 (4H, m, C$_6$H$_4$)
$^{13}$C-NMR (CDCl$_3$) δ: 8.69 (2×C), 16.32 (2×C), 27.24 (2×C), 38.44, 55.10, 77.13, 79.12 (2×C), 106.70 (2×C), 121.61, 122.35, 128.83, 134.20, 147.30, 148.51, 151.12 (2×C),

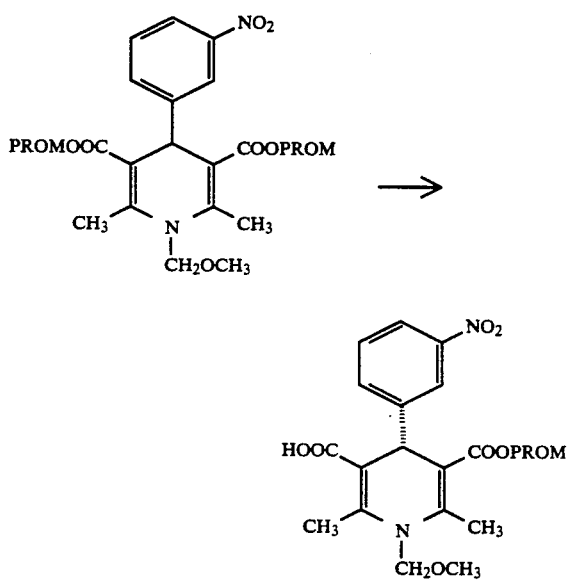

In 20 ml of isopropyl ether saturated with water was dissolved 267 mg of bis(propionyloxymethyl) 1,4-dihydro -2,6-dimethyl-1-methoxymethyl-4-(3-nitrophenyl) -3,5-pyridinedicarboxylate obtained in Example 12, and 50 mg of Lipase B was added thereto, followed by stirring at 0° to 5° C. for 8 hours. Any insoluble matter was removed by filtration and washed with dichloromethane. The filtrate was concentrated under reduced pressure, and the residue was subjected to silica gel column chromatography (ethyl acetate/hexane=½) to obtain 155 mg (yield: 71%) of (S)-1,4-dihydro-2,6-dimethyl-1-methoxymethyl-4-(3-nitrophenyl)-5-propionyloxymethoxycarbonyl -3-pyridinecarboxylic acid as a pale yellow crystal.

Melting point: 54°-56° C. (ethyl acetate/n-hexane)
$[\alpha]_D$:+49.8° (c=0.7, acetone)
IR (nujol): 1750, 1710, 1695 cm$^{-1}$ $^1$H-NMR (CDCl$_3$) δ: 1.10 (3H, t, J=7.3Hz, CH$_2$CH$_3$), 2.31, 2.32 (2H, each q, J=7.3Hz, OCH$_2$CH$_3$), 2.55 (3H, s, CH$_3$), 2.58 (3H, s, CH$_3$), 3.34 (3H, s, OCH$_3$), 4.82 (2H, s, NCH$_2$O), 5.19 (1H, s, >CH—), 5.78 1H, d, J=5.5Hz, OCH$_A$H$_B$O), 5.84 (1H, d, J=5.5Hz, OCH$_A$H$_B$O), 7.35-7.38, 7.61-7.63, 7.99-8.01 (4H, m, C$_6$H$_4$)
$^{13}$C-NMR (CDCl$_3$) δ: 8.71, 16.30, 16.35, 27.26, 38.23, 55.09, 77.17, 79.08, 106.69, 106.85, 121.61, 122.18, 128.93, 134.19, 147.20, 148.48, 151.33, 151.62, 165.51, 172.73, 173.17

TEST EXAMPLE 5

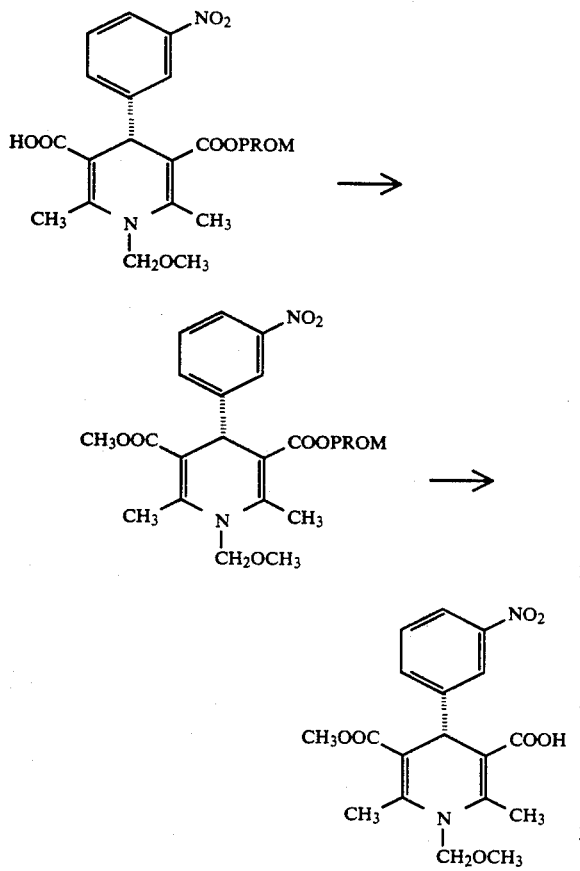

In 5 ml of dichloromlthane was dissolved 90 mg of (S)-1,4-dihydro-2,6-dimethyl-1-methoxymethyl-4-(3-nitrophenyl)-5-propionyloxymethylcarbonyl-3-pyridinecarboxylic acid obtained in Example 13, and a diazomethane diethyl ether solution was added thereto under cooling with ice, followed by stirring for 1 hour. Acetic acid was added to the reaction mixture until the yellow color disappeared, and the mixture was concentrated. The residue was subjected to silica gel column chromatography (ethyl acetate/hexane=⅓) to obtain 89 mg (yield: 96%) of (S)-methyl propionyloxymethyl 1,4-dihydro-2,6-dimethyl-1-methoxymethyl-4-(3-nitrophenyl)-3,5-pyridinedicarboxylate as a pale yellow oily substance.

$[\alpha]_D$: +32.5° (c=1.3, acetone)

IR (nujol): 1760, 1705, 1650 cm$^{-1}$ $^1$H-NMR (CDCl$_3$) δ: 1.10 (3H, t, J=7.7Hz, CH$_2$CH$_3$), 2.31, 2.32 (2H, each q, J=7.7Hz, OCH$_2$CH$_3$), 2.55 (6H, s, 2×CH$_3$), 3.33 (3H, s, OCH$_3$), 3.71 (3H, s, COOCH$_3$), 4.81 (2H, s, NCH$_2$O), 5.16 (1H, s, >CH—), 5.79 (1H, d, J=5.4Hz, OCH$_A$H$_B$O), 5.84 (1H, d, J=5.4Hz, OCH$_A$H$_B$O), 7.33–7.39, 7.56–7.58, 7.98–8.02 (4H, m, C$_6$H$_4$)

$^{13}$C-NMR (CDCl$_3$) δ: 8.71, 16.03, 16.37, 27.26, 38.54, 51.57, 55.05, 77.10, 78.95, 106.01, 107.92, 121.54, 122.27, 128.86, 133.94, 147.53, 148.47, 148.95, 151.62, 165.65, 167.48, 173.20

An aliquot of the product (non-recrystallized) was hydrolyzed and then reacted with phenyldiazomethane. The resulting (S)-benzyl methyl 1,4-dihydro-2,6-dimethyl -1-methoxymethyl-4-(3-nitrophenyl)-3,5-pyridinedicarboxylate was subjected to HPLC (isopropanol/hexane =1/10) using CHIRALCEL OD to find the optical purity to be 99% ee.

EXAMPLE 14

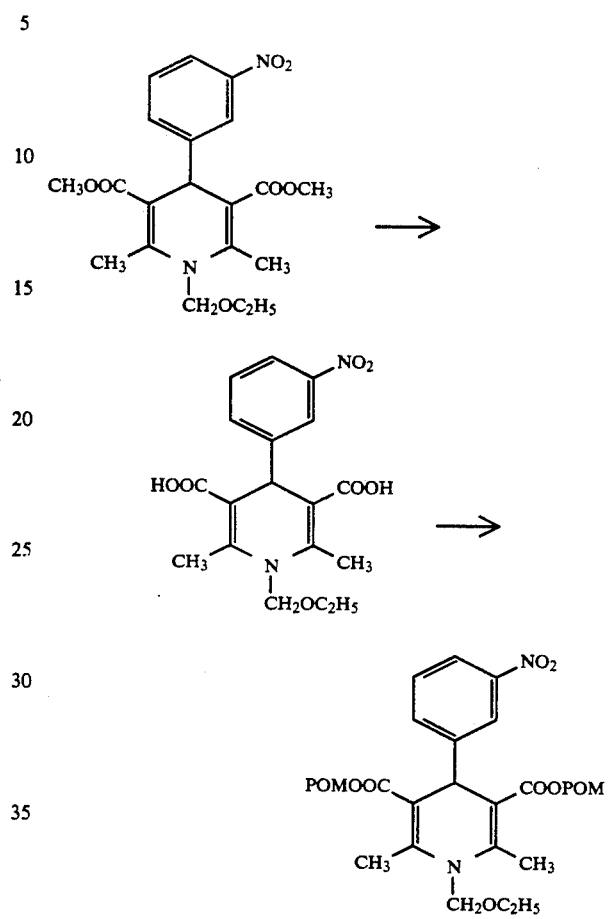

1) In methanol were dissolved 5.6 g of potassium hydroxide and 1.4 g of benzyltributylammonium bromide, and 8.0 g of dimethyl 1,4-dihydro-2,6-dimethoxy -1-ethoxymethyl-4-(3-nitrophenyl)-3,5-pyridinedicarboxylate was added to the solution, followed by refluxing for 48 hours. Ten milliliters of water were added thereto, and the solution was rendered acidic (pH=2-3) with concentrated hydrochloric acid under ice-cooling. The solution was extracted with ethyl acetate three times, and the extract was dried over anhydrous magnesium sulfate. Magnesium sulfate was removed by filtration, and the filtrate was concentrated under reduced pressure to obtain 6.2 g (yield: 82%) of 1,4-dihydro-2,6-dimethyl-1-ethoxymethyl-4-(3-nitrophenyl) -3,5-pyridinedicarboxylic acid as a pale yellow powder.

Melting point: 175°–176° C. (ethanol/n-hexane)

IR (nujol): 1665 cm$^{-1}$ $^1$H-NMR (CD$_3$OD) δ: 1.17 (3H, t, J=6.8Hz, CH$_2$CH$_3$), 2.56 (6H, s, 2×CH$_3$), 3.44 (2H, q, OCH$_2$CH$_3$), 4.95 (2H, s, NCH$_2$O), 5.22 (1H, s, >CH—), 7.41–7.47, 7.63–7.66, 7.98–8.08 (4H, m, C$_6$H$_4$)

$^{13}$C-NMR (CDCl$_3$) δ: 15.34, 16.30 (2×C), 40.39, 63.98, 76.54, 108.20 (2×C), 122.18, 123.11, 130.26, 134.89, 149.59 (2×C), 151.07 (2×C), 171.14 (2×C)

2) In 30 ml of dimethylformamide was dissolved 3.2 g of the resulting crude 1,4-dihydro-2,6-dimethyl-1-ethoxymethyl-4-(3-nitrophenyl)-3,5-pyridinedicarboxylic acid obtained in (1) above, and 1.9 g of diisopropylethylamine and 2.2 g of chloromethyl pivalate were added thereto in an argon stream, followed by stirring for 48 hours. The reaction mixture was filtered and washed with dichloromethane. The filtrate was washed successively with water and a saturated sodium chloride aqueous solution and dried over anhydrous magnesium sulfate. Magnesium sulfate was removed by filtration, and the filtrate was concentrated under reduced pressure. The residue was subjected to silica gel column chromatography (ethyl acetate/hexane=1/5) to obtain 1.8 g (yield: 44%) of bis(pivaloyloxymethyl) 1,4-dihydro-2,6-dimethyl-1-ethoxymethyl-4-(3-nitrophenyl)-3,5-pyridinedicarboxylate as a pale yellow oily substance.

IR (neat): 1750, 1715 cm$^{-1}$ $^1$H-NMR (CDCl$_3$) δ: 1.14 (18H, s, 6×CH$_3$), 1.25 (3H, t, J=6.8Hz, CH$_2$CH$_3$), 2.56 (6H, s, 2×CH$_3$), 3.51 (2H, s, CH$_2$CH$_3$), 4.88 (2H, s, NCH$_2$O), 5.16 (1H, s, >CH—), 5.73 (2H, d, J=5.4Hz, OCH$_A$H$_B$O), 5.83 (2H, d, J=5.4Hz, OCH$_A$H$_B$O), 7.30-7.39, 7.59-7.62, 7.97-8.01 (4H, m, C$_6$H$_4$)

$^{13}$C-NMR (CDCl$_3$) δ: 14.93, 16.26 (2×C), 26.77 (6×C), 38.37, 38.63 (2×C), 63.26, 75.57, 79.44 (2×C), 106.42 (2×C), 121.55, 122.09, 128.93, 134.20, 147.41, 148.46, 151.04 (2×C), 165.47 (2×C), 177.02 (2×C)

EXAMPLE 15

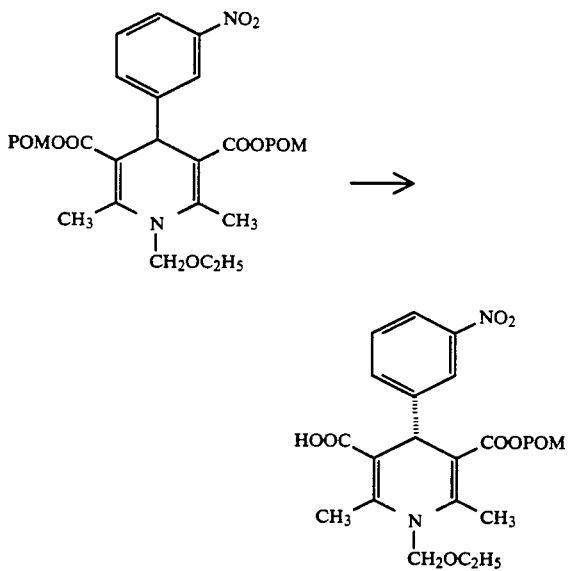

In 20 ml of isopropyl ether saturated with water was dissolved 1.2 g of bis(pivaloyloxymethyl) 1,4-dihydro-2,6-dimethyl-1-ethoxymethyl-4-(3-nitrophenyl) -3,5-pyridinedicarboxylate obtained in Example 14, and 200 mg of Lipase B was added thereto, followed by stirring at room temperature for 5 hours. Any insoluble matter was removed by filtration and washed with dichloromethane. The filtrate was concentrated under reduced pressure, and the residue was subjected to silica gel column chromatography (ethyl acetate/hexane=½) to obtain 840 mg (yield: 83%) of (S)-1,4-dihydro -2,6-dimethyl-1-ethoxymethyl-4-(3-nitrophenyl) -5-pivaloyloxymethoxycarbonyl-3-pyridinecarboxylic acid as a pale yellow crystal.

Melting point: 85°-86° C. (ethanol/n-hexane)
[α]$_D$:+37.0° (c=1.0, acetone)
IR (nujol): 1740, 1695, 1650 cm$^{-1}$ $^1$H-NMR (CDCl$_3$) δ: 1.13 (9H, s, 3×CH$_3$), 1.25 (3H, t, J=6.8Hz, CH$_2$CH$_3$), 2.57 (3H, s, CH$_3$), 2.58 (3H, s, CH$_3$), 3.50 (2H, q, J=6.8Hz, CH$_2$CH$_3$), 4.87 (2H, s, NCH$_2$O), 5.19 (1H, s, >CH—), 5.78 (1H, d, J=4.5Hz, OCH$_A$H$_B$), 5.84 (1H, d, J=5.4Hz, OCH$_A$H$_B$O), 7.33-7.39, 7.62-7.65, 7.98-8.01 (4H, m, C$_6$H$_4$)

$^{13}$C-NMR (CDCl$_3$) δ: 14.93, 16.24, 16.32, 26.77 (3×C), 38.23, 38.69, 63.27, 75.61, 79.38, 106.49 (2×C), 121.58, 122.03, 128.98, 134.20, 147.30, 148.44, 151.21, 151.64, 165.25, 165.48, 171.99

TEST EXAMPLE 6

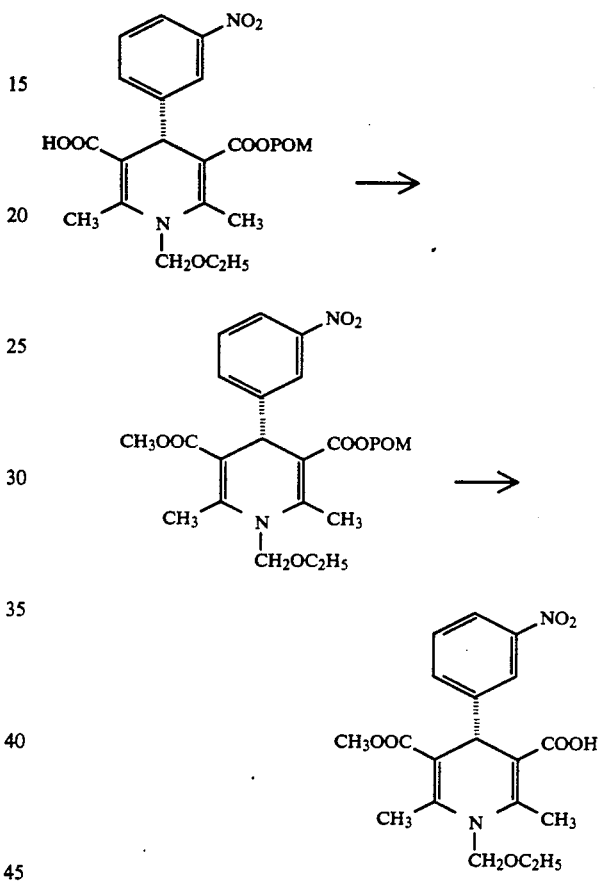

1) In 5 ml of dichloromethane was dissolved 781 mg of (S)-1,4-dihydro-2,6-dimethyl-1-ethoxymethyl-4-(3-nitrophenyl)-5-pivaloyloxymethylcarbonyl-3-pyridinecarboxylic acid obtained in Example 15, and 8 ml of a diazomethane diethyl ether solution was added thereto under ice-cooling, followed by stirring for 1 hour. Acetic acid was added to the reaction mixture until the yellow color disappeared, and the mixture was concentrated. The residue was subjected to silica gel column chromatography (ethyl acetate/hexane=½) to obtain 693 mg (yield: 86%) of (S)-methyl pivaloyloxymethyl 1,4-dihydro-2,6-dimethyl-1-ethoxymethyl-4-(3-nitrophenyl)-3,5-pyridinedicarboxylate as a pale yellow crystal.

Melting point: 81°-82° C. (ethanol/n-hexane)
[α]$_D$: +27.1° (c=1.0, acetone)
IR (nujol): 1755, 1720,1695 cm$^{-1}$ $^1$H-NMR (CDCl$_3$) δ: 1.14 (9H, s, 3×CH$_3$), 1.24 (3H, t, J=6.8Hz, CH$_2$CH$_3$)2.56 (6H, s, 2×CH$_3$), 3.49 (2H, q, J=6.8Hz, OCH$_2$CH$_3$), 3.71 (3H, s, COOCH$_3$), 4.86 (2H, s, NCH$_2$O), 5.14 (1H, s, >CH—), 5.79 (1H, d, J=5.6Hz, OCH$_A$H$_B$O), 5.83 (1H, d, J=5.6Hz, OCH$_A$H$_B$O), 7.33–7.39, 7.58–7.60, 7.98–8.01 (4H, m, C$_6$H$_4$)

$^{13}$C-NMR (CDCl$_3$) δ: 14.94, 16.01, 16.29, 26.77 (3×C), 38.49, 38.69, 51.54, 63.21, 75.53, 79.30, 105.86, 107.62, 121.51, 122.12, 128.90, 133.96, 147.62, 148.44, 149.12, 151.49, 165.62, 167.53, 177.17

In 3 ml of methanol was dissolved 300 mg of potassium hydroxide, and 104 mg of the (S)-methyl pivaloyloxymethyl 1,4-dihydro-2,6-dimethyl-1-ethoxymethyl-4-(3-nitrophenyl)-3,5-pyridinedicarboxylate obtained in (1) above was added thereto, followed by stirring for 20 hours. The reaction mixture was rendered acidic with 1N hydrochloric acid and extracted twice with dichloromethane. The extract was washed successively with water and a saturated sodium chloride aqueous solution, and dried over anhydrous magnesium sulfate. Magnesium sulfate was removed by filtration, and the filtrate was concentrated under reduced pressure. The residue was purified by silica gel column chromatography (ethyl acetate/hexane=$\frac{1}{2}$) to obtain 77 mg (yield: 95%) of (R)-1,4-dihydro-2,6-dimethyl-1-ethoxymethyl -5-methoxycarbonyl-4-(3-nitrophenyl)-3-pyridinecarboxylic acid as a pale yellow crystal.

Melting point: 134°–135° C. (ethanol/n-hexane)

[α]$_D$: −16.3° (c=1.0, acetone) (data in the literature: melting point: 134°–135° C.;

[α]$_D$: −16.0° (c=1.78, acetone), refer to M. Kajino, Y Wada, Y. Magai, A. Nagaoka, and K. Meguro, *Chem. Pharm. Bull.*, Vol. 37, p. 2225 (1989)).

IR (nujol): 1705, 1670 cm$^{-1}$ $^1$H-NMR (CDCl$_3$) δ: 1.23 (3H, t, J=6.8Hz, CH$_2$CH$_3$), 2.56 (3H, s, CH$_3$), 2.58 (3H, s, CH$_3$), 3.47 (2H, q, J=6.8Hz, OCH$_2$CH$_3$), 3.71 (3H, s, COOCH$_3$), 4.86 (2H, s, NCH$_2$O), 5.21 (1H, s, >CH—), 7.34–7.40, 7.60–7.63, 8.00–8.02 (4H, m, C$_6$H$_4$)

$^{13}$C-NMR (CDCl$_3$) δ: 14.93, 15.98, 16.37, 38.34, 51.55, 63.21, 75.56, 105.91, 107.66, 121.52, 122.10, 128.98, 133.90, 147.50, 148.40, 149.25, 152.08, 167.56, 172.42

An aliquot of the product (non-recrystallized) was reacted with phenyldiazomethane, and the resulting (S)-benzyl methyl 1,4-dihydro-2,6-dimethyl-1-ethoxymethyl-4-(3-nitrophenyl) -3,5-pyridinedicarboxylate was subjected to HPLC (isopropanol/hexane=1/10) using CHIRALCEL OD to find the optical purity to be 99% ee.

IR (neat): 1705, 1680 cm$^{-1}$ $^1$H-NMR (CDCl$_3$) δ: 1.23 (3H, t, J=6.8Hz, CH$_2$CH$_3$), 2.54 (3H, s, CH$_3$), 2.55 (3H, s, CH$_3$), 3.47 (2H, q, J=6.8Hz, OCH$_2$CH$_3$), 3.69 (3H, s, COOCH$_3$), 4.85 (2H, s, NCH$_2$O), 5.09 (1H, d, J=12.7Hz, OCH$_A$H$_B$Ph), 5.19 (1H, s, >CH—), 5.22 (1H, d, J=12.7Hz, OCH$_A$H$_B$Ph), 7.19–7.38, 7.48–7.51, 7.95–7.99 (9H, m, C$_6$H$_4$ and C$_6$H$_5$)

$^{13}$C-NMR (CDCl$_3$) δ: 14.94, 16.09, 16.18, 38.89, 51.48, 63.15, 66.21, 75.50, 107.05, 107.27, 121.40, 122.32, 128.09 (2×C), 128.12 (2×C), 128.49, 128.84, 133.93, 136.11, 147.92, 148.31, 149.19, 149.73, 167.06, 167.73

EXAMPLE 16

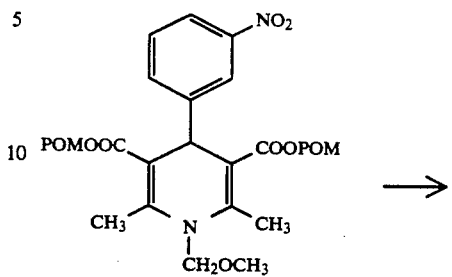

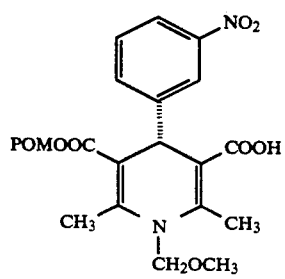

POM = CH$_2$OCOC(CH$_3$)$_3$

In 20 ml of isopropyl ether saturated with water was dissolved 590 mg of bis(pivaloyloxymethyl) 1,4-dihydro-2,6-dimethyl-1-methoxymethyl-4-(3-nitrophenyl) -3,5-pyridinedicarboxylate obtained in Example 1 or 2, and 200 mg of Lipase PS was added thereto, followed by stirring at room temperature for 72 hours. Any insoluble matter was removed by filtration and washed with dichloromethane. The filtrate was concentrated under reduced pressure, and the residue was purified by silica gel column chromatography (ethyl acetate/hexane=$\frac{1}{2}$) to obtain 210 mg (yield: 44%) of (R)-1,4-dihydro-2,6-dimethyl-1-methoxymethyl -4-(3-nitrophenyl)-5-pivaloyloxymethoxycarbonyl -3-pyridinecarboxylic acid as a pale yellow crystal.

[α]$_D$:−28.7° (c=1.3, acetone)

Various spectral data of the product were in complete agreement with those of the (S)-compound obtained in Example 3.

The resulting (R)-1,4-dihydro-2,6-dimethyl-1-methoxymethyl-4-(3-nitrophenyl)5-pivaloyloxymethoxycarbonyl -3-pyridinecarboxylic acid was treated with a 0.5 M solution of diazomethane in diethyl ether and then treated with a 10% potassium hydroxide solution in methanol. The resulting (S) -1,4-dihydro-2,6-dimethyl-1-methoxymethyl-4-(3-nitrophenyl)-5-methoxycarbonyl-3-pyridinecarboxylic acid (recrystallized) was reacted with phenyldiazomethane to obtain (R)-benzyl methyl 1,4-dihydro-2,6-dimethyl-1-methoxymethyl-4-(3-nitrophenyl)-3,5-pyridinedicarboxylate. As a result of HPLC (isopropanol/hexane=1/10) using CHIRALCEL OD, the optical purity was found to be 69% ee.

EXAMPLE 17

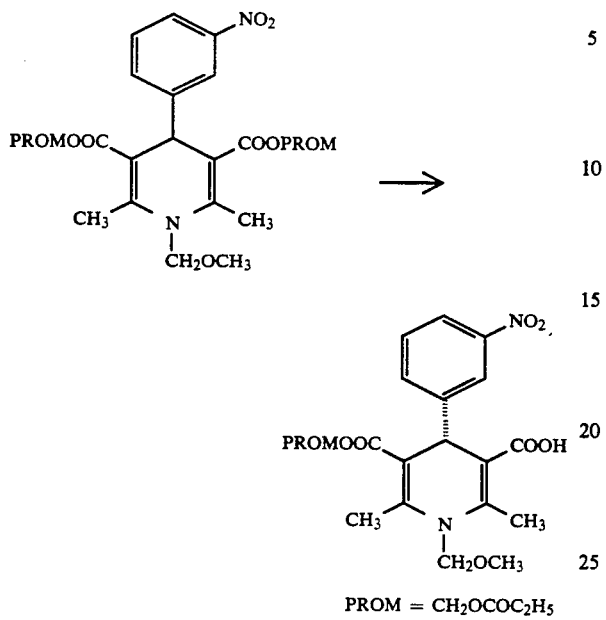

PROM = CH₂OCOC₂H₅

In 20 ml of isopropyl ether saturated with water was dissolved 120 mg of bis(propionyloxymethyl) 1,4-dihydro -2,6-dimethyl-1-methoxymethyl-4-(3-nitrophenyl) -3,5-pyridinedicarboxylate obtained in Example 12, and 50 mg of Lipase PS was added thereto, followed by stirring at room temperature for 72 hours. Any insoluble matter was removed by filtration and washed with dichloromethane. The filtrate was concentrated under reduced pressure, and the residue was purified by silica gel column chromatography (ethyl acetate/hexane=½) to obtain 77 mg (yield: 78%) of (R)-1,4-dihydro-2,6-dimethyl-1-methoxymethyl -4-(3-nitrophenyl)-5-propionyloxymethoxycarbonyl -3-pyridinecarbox-ylic acid as a pale yellow crystal.

$[\alpha]_D$: −42.1° (c=1.5, acetone)

Various spectral data of the product were in complete agreement with those of the (S)-compound obtained in Example 13.

The resulting (R)-1,4-dihydro-2,6-dimethyl-1-methoxymethyl-4-(3-nitrophenyl)-5-propionyloxymethoxycarbonyl-3-pyridinecarboxylic acid was treated with a 0.5 M solution of diazomethane in diethyl ether and then with a 10% methanol solution of potassium hydroxide to obtain (S)-1,4-dihydro -2,6-dimethyl-1-methoxymethyl-4-(3-nitrophenyl -5-methoxycarbonyl-3-pyridinecarboxylic acid (recrystallized), which was then reacted with phenyldiazomethane to obtain (R)-benzyl methyl 1,4-dihydro-2,6-dimethyl-1-methoxymethyl -4-(3-nitrophenyl)-3,5-pyridinedicarboxylate. As a result of HPLC (isopropanol/hexane−1/10) using CHIRALCEL OD, the optical purity was found to be 88% ee.

EXAMPLE 18

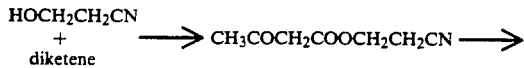

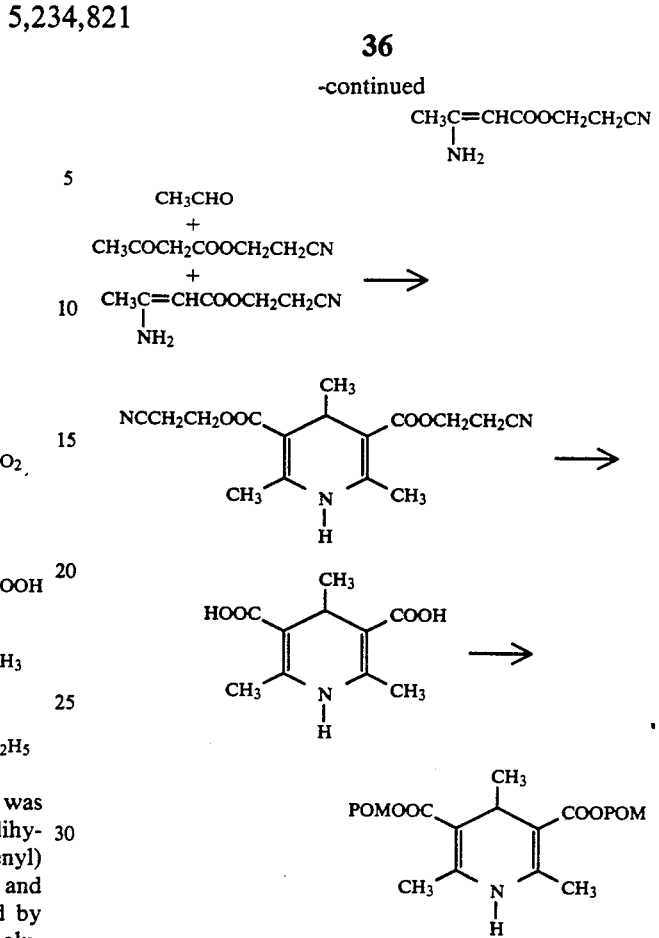

1) In 37.5 g of 95% ethylene cyanohydrin was dissolved 100 mg of 4-dimethylaminopyridine, and 38.6 ml of diketene was added thereto dropwise at 70° to 80° C. for one hour under stirring, following by stirring at 70° to 80° C. for 2 hours. Sixty two grams of the resulting crude 2-cyanoethyl acetoacetate was dissolved in 400 ml of tetrahydrofuran. To the solution was added 20 g of molecular sieves 4A, following by blowing an ammonia gas for 2 hours with stirring under ice-cooling. The resulting solution was stirred in a container closed with a rubber stopper at a room temperature for 18 hours. Molecular sieves 4A was removed by filtration, and the filtrate was concentrated under reduced pressure to obtain a yellow crystal. Recrystallization from ethyl acetate/n-hexane gave 22.2 g (yield: 36%) of 2-cyanoethyl 3-aminocrotonate as a pale yellow crystal.

In 45 ml of isopropyl alcohol was dissolved 11.0 g of 90% acetaldehyde, 11.6 g of the 2-cyanoethyl acetoacetate obtained above, and 11.6 g of the 2-cyanoethyl 3-aminocrotonate obtained above, and the mixture was stirred in a closed tube at 90° C. for 18 hours. After the reaction, the reaction solution was concentrated under reduced pressure. The residue was purified by silica gel column chromatography (dichloromethane) to obtain a crude product. Recrystallization from ethanol/n-hexane gave 14.5 g (yield: 61%) of dicyanoethyl 1,4-dihydro-2,4,6-trimethyl-3,5-pyridinedicarboxylate as a yellows needle-like crystal.

Melting point: 125°–126° C. (Ethanol/n-hexane)
IR (nujol) 3352, 2250, 1699 cm⁻¹
¹H-NMR (CDCl₃) δ: 1.02 (3H, d, J=6.4Hz, CH₃), 2.30 (6H, s, 2×CH₃), 2.76 (4H, t, J=6.4Hz, 2×CH₂CN), 3.85 (1H, q, >CH—, J=6.4Hz), 4.32 (2H, dt, J=11.2, 6.4Hz, OCH$_A$H$_B$), 4.38 (2H, dt, J=11.2, 6.4Hz, OCH$_A$H$_B$), 5.88 (1H, s, NH)

$^{13}$C-NMR (CDCl$_3$) δ: 18.21 (2×C), 19.59 (2×C), 22.39, 28.22, 58.14 (2×C), 108.78 (2×C), 117.21 (2×C), 145.98 (2×C), 166.70 (2×C)

2) In 120 ml of acetone containing 240 ml of 1N sodium hydroxide was dissolved 12.7 g of the dicyanoethyl 1,4-dihydro-2,4,6-trimethyl-3,5-pyridinedicarboxylate obtained in (1) above, and the solution was stirred at a room temperature for 2 hours. After the reaction, the reaction mixture was diluted with 240 m; of water and washed twice with dichloromethane. The separated aqueous layer was rendered acidic (pH=1-2) with concentrated hydrochloric acid under ice-cooling and stirred for 3 hours. The thus formed crystal was collected by suction filtration. The filtrate was dried under reduced pressure to yield 4.55 g (yield: 54%) of 1,4-dihydro -2,4,6-trimethyl-3,5-pyridinedicarboxylic acid as a pale yellows powder.

IR (nujol) 3424, 1685 cm$^{-1}$ $^1$H-NMR (CD$_3$OD) δ: 0.92 (3H, d, J=6.6Hz, CH$_3$), 2.24 (6H, s, 2×CH$_3$, 3.76 (1H, q, J=6.6Hz, >CH—)

$^{13}$C-NMR (CD$_3$OD) δ: 18.72 (2×C), 22.31, 30.04, 104.50 (2×C), 147.73 (2×C), 171.95 (2×C)

3) In 60 ml of dimethylformamide was dissolved 4.22 g of the 1,4-dihydro-2,4,6-trimethyl-3,5-pyridinedicarboxylic acid obtained in (2) above, and 2.4 g of 60% oily sodium hydride was added thereto at 0° C. in an argon stream with stirring. After stirring for 30 minutes, 7.23 g of chloromethyl pivalate was added thereto dropwise under ice-cooling, followed by stirring at room temperature for 18 hours. Acetic acid (about 3 ml) was added to the reaction mixture until the foaming stopped. The mixture was diluted with dichloromethane, washed successively with water, a saturated sodium hydrogen carbonate aqueous solution and a saturated sodium chloride aqueous solution, and dried over anhydrous sodium sulfate. Sodium sulfate was removed by filtration, and the filtrate was concentrated under reduced pressure. The residue was subjected to silica gel column chromatography (ethyl acetate/hexane ⅓) to obtain 3.69 g (yield: 42%) of bis(pivaloyloxymethyl) 1,4-dihydro-2,4,6-trimethyl -3,5-pyridinedicarboxylate as a colorless crystal.

Melting point 82°–83° C. (Ethanol/n-hexane)

IR (nujol) 3332, 1749, 1713 cm$^{-1}$ $^1$H-NMR (CDCl$_3$) δ: 0.95 (3H, d, J=6.4Hz, CH$_3$), 1.21 (18H, s, 6×CH$_3$), 2.27 (6H, s, 2×CH$_3$), 3.81 (1H, q, J=6.4Hz, >CH—), 5.80 (2H, d, J=5.4Hz, OCH$_A$H$_B$)), 5.89 (2H, d, J=5.4Hz, OCH$_A$H$_B$O), 6.17 (1H, s, NH)

$^{13}$C-NMR (CDCl$_3$) δ: 19.57 (2×C), 22.45, 26.89 (9×C), 28.15, 38.80 (2×C), 79.29 (2×C), 103.72 (2×C), 146.40 (2×C), 165.96 (2×C), 177.35 (2×C)

EXAMPLE 19

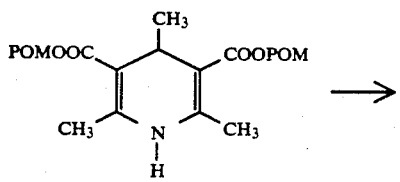

-continued

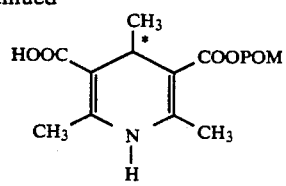

In 30 ml of isopropyl ether saturated with water was dissovled 1.32 g of the bis(pivaloyloxymethyl) 1,4-dihydro -2,4,6-trimethyl-3,5-pyridinedicarboxylate obtained in Example 18, and 300 mg of Lipase B was added thereto, followed by stirring at room temperature for 8 horus. Any insoluble matter was removed by filtration and washed with acetone. The filtrate was concentrated under reduce dpressure. The residue was subjected to silica gel column chromatography (ethyl acetate/hexane=1/3) to obtain 741 mg (yield: 76%) of (+)-1,4-dihydro -2,4,6-trimethyl-5-pivaloyloxymethoxycarbonyl -3-pyridinecarboxylic acid as a pale yellow crystal.

[α]$_D$25.8° (c=1.0, Acetone

Melting point: 113°–1142 C. (ethyl acetate/n-hexane)

IR (nujol) 3350, 1755, 1690 cm$^{-1}$ $^1$H-NMR (Acetone-d$_6$)δ: 0.94 (3H, d, J=6.4HZ, CH$_3$), 1.19 (9H, s, 3×CH$_3$), 2.27 (6H, s, 2×CH$_3$), 3.85 (1H, q, J=6.4Hz, >Ch—), 5.79 (1H, d, J=5.5Hz, OCH$_A$H$_B$O), 5.87 (1H, d, J=5.5Hz, OCH$_A$H$_B$O), 7.91 (1H, s, NH)

$^{13}$C-NMR (Acetone-d$_6$) δ: 18.66, 19.99, 27.14 (3×C), 27.50, 39.29, 79.77, 102.80, 104.65, 146.18, 148,70, 166.51, 169.19, 179.36

TEST EXAMPLE 7

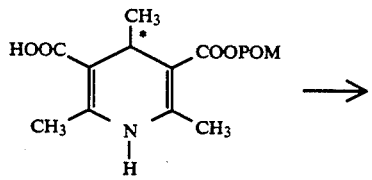

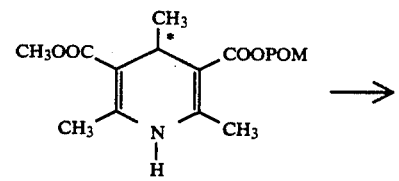

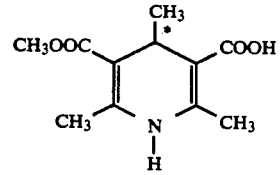

1) In 2 ml of acetone was dissovled 325 mg of the (+)-1,4-dihydro-2,4,6-trimethyl -5-pivaloyloxymethoxycarbonyl-3-pryidenecarboxylic acid obtained in Example 19, and 2 ml of a diazomethane solution in diethyl ether was added thereto under ice-cooling, followed by stirring for 1 hour. Acetic acid was added to the reaction mixture until the yellow color disappeared, and the mixture was concentrated. The residue was purified by silica gel column chromatography (ethyl acetate/hexane=⅓) to obtain 223 mg (yield: 66%) of (+)-methyl pivaloyloxymethyl 1,4-dihydro-2,4,6-trimethyl-3,5-pyridinedicarboxylate as a colorless crystal. HPLC (isopropanol/hexane=1/15) using CHIRALCEL OJ revealed that the product had an optical purity of 91% ee. Recrystallization from ethyl acetato/n-hexane gave 186 mg (yield: 83%, ×99% ee) of a colorless cyrstal.

$[\alpha]_D + 18.0°$ C. (c=1.0, Acetone)

Melting point: 113°-114° C. (ethyl acetate/n-hexane)

IR (njuol) 33,58, 1699 cm$^{-1}$ $^1$H-NMR (CDCl$_3$) δ: 0.95 (3H, d, J=6.8Hz, CH$_3$), 1.21 (9H, s, 3×CH$_3$), 2.27 (6H, s, 2×CH$_3$), 3.72 (3H, s, COOCH$_3$), 3.83 (1H, q, J=6.8Hz, >CH—), 5.62 (1H, s, NH), 5.81 (1H, d, J=5.4Hz, OCH$_A$H$_B$O), 5.89 (1H, d, J=5.4Hz, OCH$_A$H$_B$O)

$^{13}$C-NMR (CDCl$_3$) δ:19.30, 19.82, 22.37, 26.89 (3×C), 28.28, 38.80, 51.42, 79.13, 103.29, 105.10, 144.21, 146.58, 166.05, 168.11, 177.40

2) In 36 mg (0.64 mmol) of potassium hydroxide in 2 ml of methanol was further dissolved 145 mg of (+)-methyl pivaloyloxymethyl 1,4-dihydro-2,4,6-trimethyl-3,5-pyridinedicarboxylate obtained in (1) above, and the solution was stirred for 18 hours. The reaction mixture was neutralized with 1N hydrochloric acid under ice-cooling, and then concentrated under reduced pressure. The residue was extracted 5 times with dichloromethane, washed with a saturated sodium chloride aqueous solution, and dried over anhydrous magnesium sulfate. Magnesium sulfate was removed by filtration, and the filtrate was concentrated under reduced pressure. The residue was subjected to silica gel column chromatography (ethyl acetate/hexane =½) to obtain 80 mg (yield: 80%) of (−)-1,4-dihydro-5-methoxycarbonyl -2,4,6-trimethyl-3-pyridinecarboxylic acid as a colorless crystal.

$[\alpha]_D - 21.5°$ (c=0.2, Acetone)

Melting point: 165°-166° C.

IR (nujol) 3350, 1690 cm$^{-1}$ $^1$H-NMR (Acetone-d$_6$) δ: 0.94 (3H, d, J=6.4Hz, CH$_3$), 2.26 (3H, s, CH$_3$), 2.27 (3H, s, CH$_3$), 3.66 (3H, s, COOCH$_3$), 3.85 (1H, q, J=6.4Hz, >CH—), 7.75 (1H, s, NH)

$^{13}$C-NMR (Acetone-d$_6$) δ: 18.66, 18.76, 22.62, 29.48, 50.86, 104.07, 104.14, 146.48, 146.62, 168.46, 169.43

EXAMPLE 20

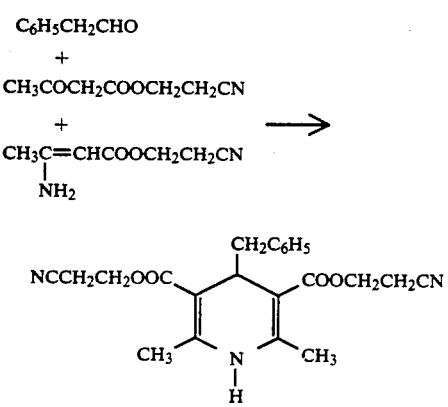

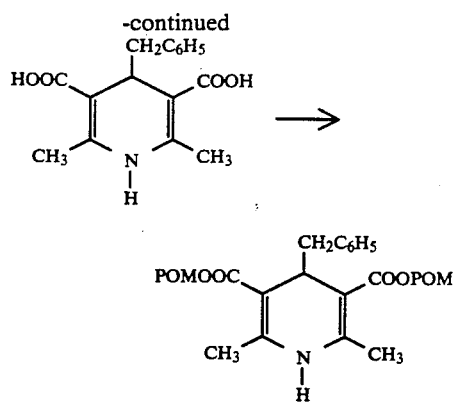

The same procedure as in Example 18 was repeated except for using benzyl aldehyde instead of acetaldehyde to obtain dicyanoethyl 4-benzyl-1,4-dihyro-2,6-dimethyl -3,5-pyridinedicarboxylate in a 40% yield, 4-benzyl -1,4-dihydro-2,6-dimethyl-3,5-pyridinedicarboxylic acid in a 62% yield, and bis(pivaloyloxymethyl) 4-benzyl-1,4-dihydro-2,6-dimethyl-3,5-pyridinedicarboxylate in a 55% yield.

EXAMPLE 21

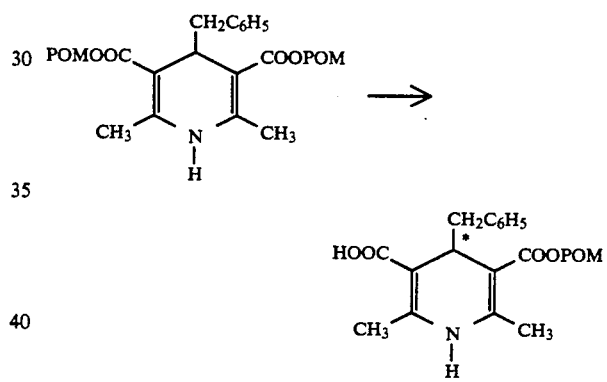

The same procedure as in Example 19 was repeated except for using the bis(pivaloyloxymethyl) 4-benzyl-1,4-dihydro-2,6-dimethyl-3,5-pyridinedicarboxylate obtained in Example 20 instead of bis(pivaloyloxymethyl) 1,4-dihydro -2,4,6-trimethyl-3,5-pyridinedicarboxylate to obtain (+) -4-benzyl-1,4-dihydro-2,6-dimethyl-5-pivaloyloxymethoxycarbonyl-3-pyridinecarboxylic acid in a 65% yield.

TEST EXAMPLE 8

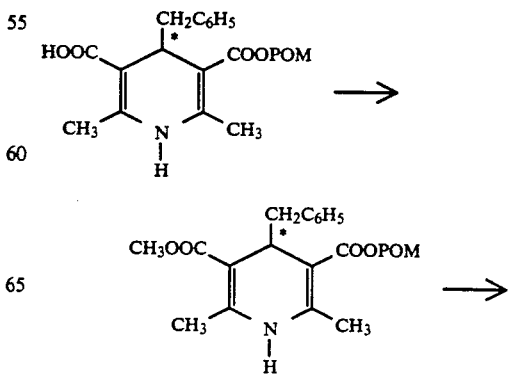

-continued

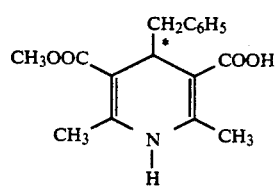

The same procedure as in Test Example 7 was repeated except for using the (+)-4-benzyl-1,4-dihydro-2,6-dimethyl-5-pivaloyloxymethoxycarbonyl-3-pyridinecarboxylic acid obtained in Example 21 instead of (+) -1,4-dihydro-2,4,6-trimethyl-5-pivaloyloxymethoxycarbonyl-3-pyridinecarboxylic acid to obtain (+)-methyl pyvaloyloxymethyl 4-benzyl-1,4-dihydro-5-methoxycarbonyl-2,6-dimethyl-3-pyridinecarboxylic acid in a 81% yield.

EXAMPLE 22

C$_6$H$_{11}$CHO
+
CH$_3$COCH$_2$COOCH$_2$CH$_2$CN
+
CH$_3$C=CHCOOCH$_2$CH$_2$CN
|
NH$_2$
→

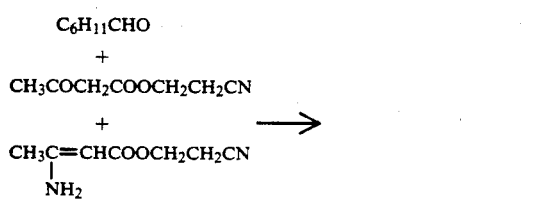

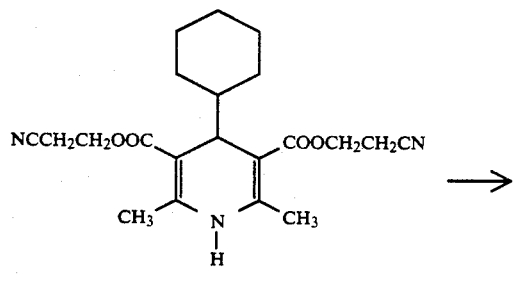

The same procedure as in Example 18 was repeated except for using cyclohexyl aldehyde instead of acetaldehyde to obtain dicyanoethyl 4-cyclohexyl-1,4-dihydro-2,6-dimethyl-3,5-pyridinedicarboxylate in a 80% yield, 4-cyclohexyl-1,4-dihydro -2,6-dimethyl-3,5- pyridinedicarboxylic acid in a 78% yield, and bis(-pivaloyloxymethyl) 4-cyclohexyl-1,4-dihydro-2,6-dimethyl-3,5-pyridinedicarboxylate in a 53% yield.

EXAMPLE 23

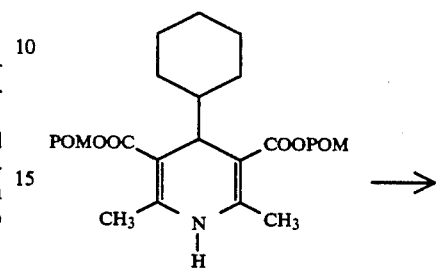

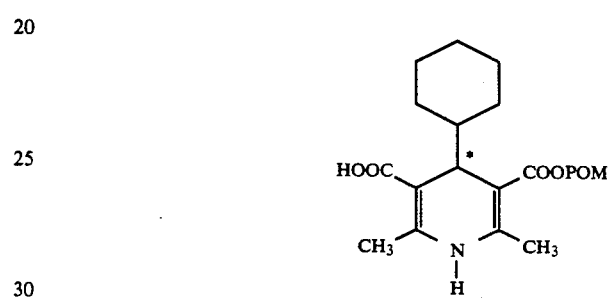

The same procedure as in Example 19 was repeated except for using the bis(pivaloyloxymethyl) 4-cyclohexyl -1,4-dihydro-2,6-dimethyl-3,5-pyridinedicarboxylate obtained in Example 22 instead of bis(pivaloyloxymethyl) 1,4-dihydro-2,4,6-trimethyl-3,5-pyridinedicarboxylate to obtain (+)-4-cyclohexyl-1,4-dihydro-2,6-dimethyl-5-pivaloyloxymethoxycarbonyl-3-pyridinecarboxylic acid in a 75% yield.

TEST EXAMPLE 9

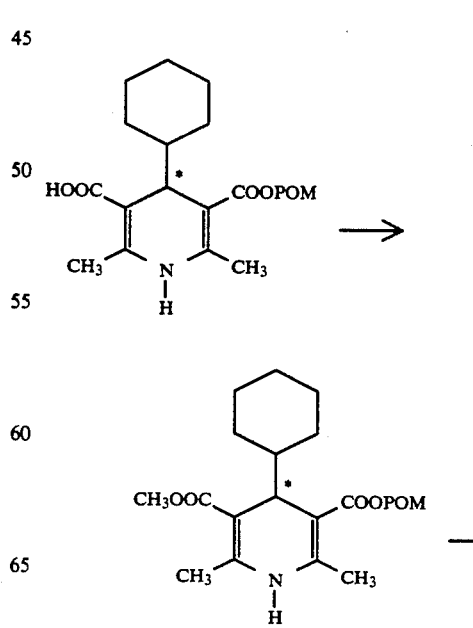

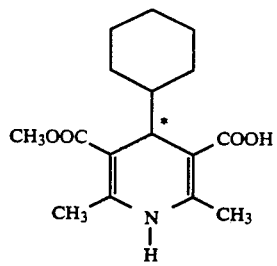

The same procedure as in Test Example 7 was repeated except for using the (+)-4-cyclohexyl-1,4-dihydro -2,6-dimethyl-5-pivaloyloxymethoxycarbonyl-3-pyridinecarboxylic acid obtained in Example 23 instead of (+)-1,4-dihydro-2,4,6-trimethyl-5-pivaloyloxymethoxycarbonyl-3-pyridinecarboxylic acid to obtain (+)-methyl pyvaloyloxymethyl 4-cyclohexyl -1,4-dihydro-5-methoxycarbonyl-2,6-dimethyl-3-pyridinecarboxylic acid in a 84% yield.

While the invention has been described in detail and with reference to specific examples thereof, it will be apparent to one skilled in the art that various changes and modifications can be made therein without departing from the spirit and scope thereof.

What is claimed is:

1. A process for preparing a 1,4-dihydropyridinemonocarboxylic acid derivative represented by formula (II):

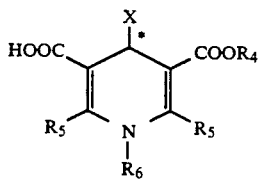 (II)

wherein X represents an alkyl group, or a group of

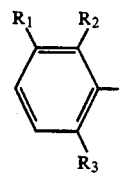

in which $R_1$, $R_2$, and $R_3$ may be the same or different and each represent a hydrogen atom, a hologen atom, a nitro group, a nitrile group, or a trifluoromethyl group; $R_4$ represents a substituted or unsubstittuted acyloxymethyl group, an alkoxycarbonyloxymethyl group, a (2-oxo-1,3-dioxolen-4-yl) methyl group, a (5-substituted-2-oxy-1,3-dioxyolen 4-yl)methyl group, or an acyl group; $R_5$ represents a lower alkyl group or a substituted alkyl group; $R_6$ represents a hydrogen, atom, a lower alkoxymethyl group, or a lower acyloxymethyl group; and * indicates an opticlaly active site, comprising reacting a 1,4-dihydropyridine derivative represented by formula (I):

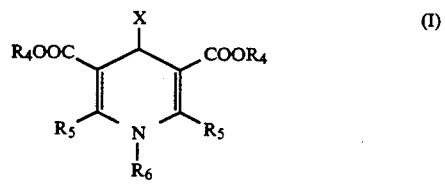 (I)

wherein X, $R_4$, $R_5$, and $R_6$ are as defined above, with a lipase originated from a microorganism belonging to the genus Pseudomonas.

2. A process as claimed in claim 1, wherein said lipase is originated from *Pseudomonas cepacia*.

3. A process as claimed in claim 1, wherein said lipase is originated from *Pseudomonas fragi*.

4. A process as claimed in claim 1, wherein said lipase is Lipase PS.

5. A process as claimed in claim 1, wherein said lipase is Lipase B.

* * * * *